United States Patent
Anderson et al.

(10) Patent No.: US 9,974,302 B2
(45) Date of Patent: May 22, 2018

(54) PESTICIDAL TOXIN ACTIVE AGAINST COLEOPTERAN AND/OR HEMIPTERAN INSECTS

(71) Applicants: Heather M. Anderson, Wildwood, MO (US); David J. Bowen, Glencoe, MO (US); Catherine A. Chay, Ballwin, MO (US); Stanislaw Flasinski, Chesterfield, MO (US); Uma R. Kesanapalli, Chesterfield, MO (US); Jason S. Milligan, Troy, IL (US); Rachael N. Slightom, Maplewood, MO (US); Yong Yin, Creve Coeur, MO (US)

(72) Inventors: Heather M. Anderson, Wildwood, MO (US); David J. Bowen, Glencoe, MO (US); Catherine A. Chay, Ballwin, MO (US); Stanislaw Flasinski, Chesterfield, MO (US); Uma R. Kesanapalli, Chesterfield, MO (US); Jason S. Milligan, Troy, IL (US); Rachael N. Slightom, Maplewood, MO (US); Yong Yin, Creve Coeur, MO (US)

(73) Assignee: Monsanto Technology LLC, St. Louis, MO (US)

( * ) Notice: Subject to any disclaimer, the term of this patent is extended or adjusted under 35 U.S.C. 154(b) by 295 days.

(21) Appl. No.: 14/455,011

(22) Filed: Aug. 8, 2014

(65) Prior Publication Data

US 2015/0047076 A1 Feb. 12, 2015

Related U.S. Application Data

(60) Provisional application No. 61/864,045, filed on Aug. 9, 2013.

(51) Int. Cl.
| | |
|---|---|
| C12N 15/82 | (2006.01) |
| C07K 14/325 | (2006.01) |
| A01N 37/18 | (2006.01) |
| A01N 37/46 | (2006.01) |
| A01N 63/02 | (2006.01) |

(52) U.S. Cl.
CPC ............ *A01N 37/18* (2013.01); *A01N 37/46* (2013.01); *A01N 63/02* (2013.01); *C07K 14/325* (2013.01); *C12N 15/8286* (2013.01); *Y02A 40/162* (2018.01)

(58) Field of Classification Search
None
See application file for complete search history.

(56) References Cited

U.S. PATENT DOCUMENTS

| | | | | |
|---|---|---|---|---|
| 6,248,536 | B1* | 6/2001 | Donovan | C07K 14/325 435/320.1 |
| 6,468,523 | B1* | 10/2002 | Mettus | C07K 14/325 424/93.2 |
| 6,593,293 | B1* | 7/2003 | Baum | C07K 14/325 514/4.5 |
| 7,662,940 | B1* | 2/2010 | Baum | C07K 14/325 536/23.1 |
| 8,461,421 | B2* | 6/2013 | Sampson | C07K 14/325 435/252.3 |
| 2004/0133942 | A1* | 7/2004 | Miles | A01N 37/46 800/279 |
| 2006/0191034 | A1* | 8/2006 | Baum | A01N 63/02 800/279 |
| 2008/0295207 | A1* | 11/2008 | Baum | A01N 63/00 800/302 |
| 2013/0097735 | A1* | 4/2013 | Bowen | C12N 15/8286 800/302 |
| 2013/0116170 | A1 | 5/2013 | Graser et al. | |
| 2013/0269060 | A1* | 10/2013 | Baum | C12N 15/8286 800/279 |

FOREIGN PATENT DOCUMENTS

WO 2009158470 A2 12/2009

OTHER PUBLICATIONS

Pardo Lopez et al, Peptides (2009) 30:589-595.*
Aronson et al, FEMS Microbiol. Lett. (2001) 195:1-8.*
Herrero et al., Biochem. J. (2004) 384:507-513.*
Abdul-Rauf et al, Curr. Microbiol. (1999) 39:94-98.*
De Maagd, et al, Trends Genet. (2001) 17:193-199.*
Okumura et al, J. Agric. Food Chem. (2005) 53:6313-6318.*
Ohba et al, Anticancer Research (2009) 29:427-434.*
Accession No. AB180980, May 26, 2006.

* cited by examiner

*Primary Examiner* — Mykola V Kovalenko
(74) *Attorney, Agent, or Firm* — Thompson Coburn LLP; J. Wendy Davis

(57) ABSTRACT

The present invention provides novel insecticidal proteins active against a Coleopteran and/or Hemipteran species pest, which include, but are not limited to, TIC3131, TIC3400 and TIC3407 proteins. The present invention also provides a DNA construct comprising operably linked to a heterologous promoter a polynucleotide that encodes the novel insecticidal protein or an insecticidal fragment thereof. The present invention further provides transgenic plants/plant cells/plant parts expressing the insecticidal proteins, methods for detecting the presence of the polynucleotide or the protein in a biological sample, and methods of controlling a Coleopteran and/or Hemipteran species pest using the insecticidal proteins.

8 Claims, No Drawings

SEQUENCE LISTING

<160> NUMBER OF SEQ ID NOS: 21

<210> SEQ ID NO 1
<211> LENGTH: 810
<212> TYPE: DNA
<213> ORGANISM: Bacillus thuringiensis

<400> SEQUENCE: 1

```
atggcgatta taaatctttt gaatgaaata agaatttggg gagaaagagc tgccagagac        60
aggaacacaa ctcttaaaag ttcaggatat ttggctagta gtccaggaag aatatataat       120
tataacatgt ctgtgccaga tcctgtagtg actgataatc ctactaatgc agctttggct       180
aggggggacca cgccaaatcc tactactcag cctatagtca gaacgattac atttaatgaa      240
acacttactg attcacagtc tacaacaaca gaacatggca taacagctgg agtaagtgcg       300
acagtaaaaa gtgaggcggg atttgttttt gcaaaggtcg gttttgaagt tacggtttca       360
tttcaatata attacacaac ttcaaacaca tatacgacag aaacatctcg aagttggact       420
gattcgcttc aaatcacagt tccccaggt tatgtaacgg aacatacatt tattgtgcaa        480
actggtccat ttagtaaaaa tgtagttttg gagtgtgata tagatggata tgcacagatc       540
tggtttgcca acggttctgg gatcacttta ggtgtgtcgc aagtcttact cgaaaatagt       600
gttccaggca ttcgctggtt aggaggatat gttactcgtt tcacaggttc aggaaagttg       660
acaggcaaaa tgggacttca atcctttgtc aatgttgtag aacgtccttt atcaggtcgt       720
gcaggacagg ttcgagaata ccaaatccca gttacaggaa aagcggact agatattcct        780
attttttgatt caatcgtatc tcgtcagtag                                       810
```

<210> SEQ ID NO 2
<211> LENGTH: 269
<212> TYPE: PRT
<213> ORGANISM: Bacillus thuringiensis

<400> SEQUENCE: 2

```
Met Ala Ile Ile Asn Leu Leu Asn Glu Ile Arg Ile Trp Gly Glu Arg
1               5                   10                  15

Ala Ala Arg Asp Arg Asn Thr Thr Leu Lys Ser Ser Gly Tyr Leu Ala
            20                  25                  30

Ser Ser Pro Gly Arg Ile Tyr Asn Tyr Asn Met Ser Val Pro Asp Pro
        35                  40                  45

Val Val Thr Asp Asn Pro Thr Asn Ala Ala Leu Ala Arg Gly Thr Thr
    50                  55                  60

Pro Asn Pro Thr Thr Gln Pro Ile Val Arg Thr Ile Thr Phe Asn Glu
65                  70                  75                  80

Thr Leu Thr Asp Ser Gln Ser Thr Thr Thr Glu His Gly Ile Thr Ala
                85                  90                  95

Gly Val Ser Ala Thr Val Lys Ser Glu Ala Gly Phe Val Phe Ala Lys
            100                 105                 110

Val Gly Phe Glu Val Thr Val Ser Phe Gln Tyr Asn Tyr Thr Thr Ser
        115                 120                 125

Asn Thr Tyr Thr Thr Glu Thr Ser Arg Ser Trp Thr Asp Ser Leu Gln
    130                 135                 140
```

```
Ile Thr Val Pro Pro Gly Tyr Val Thr Glu His Thr Phe Ile Val Gln
145                 150                 155                 160

Thr Gly Pro Phe Ser Lys Asn Val Val Leu Glu Cys Asp Ile Asp Gly
            165                 170                 175

Tyr Ala Gln Ile Trp Phe Ala Asn Gly Ser Gly Ile Thr Leu Gly Val
        180                 185                 190

Ser Gln Val Leu Leu Glu Asn Ser Val Pro Gly Ile Arg Trp Leu Gly
    195                 200                 205

Gly Tyr Val Thr Arg Phe Thr Gly Ser Gly Lys Leu Thr Gly Lys Met
210                 215                 220

Gly Leu Gln Ser Phe Val Asn Val Glu Arg Pro Leu Ser Gly Arg
225                 230                 235                 240

Ala Gly Gln Val Arg Glu Tyr Gln Ile Pro Val Thr Gly Arg Ser Gly
            245                 250                 255

Leu Asp Ile Pro Ile Phe Asp Ser Ile Val Ser Arg Gln
            260                 265

<210> SEQ ID NO 3
<211> LENGTH: 810
<212> TYPE: DNA
<213> ORGANISM: Bacillus thuringiensis

<400> SEQUENCE: 3
atggcgatta tagacctttt gaaggaaata aaaatttggg gagaaagagc tgcaaaacaa      60
cacaacacaa cacttaaaag ttcaggatat ttgggtaggg atccaggaaa tatatataat     120
tataacatga aggtaccaga tcctattgtg actgataacc ctacaaattc agcttatgcg     180
aagggaacca cgccaaatcc tacttctcag cccatagtca gaacgattac atttaatgaa     240
acacttactg attcacagtc taccacaaca gaacatggca taacagctgg agcaagtgtg     300
acagtaaaaa gtgaagcggg attactttt gcaaaagtag gtgtggaggc cacggtttca     360
tttgaataca attatacgaa ttcacagaca aaaacaacag aagtatctcg aagttggagt     420
gattcacttc agatcacagt tcctccaggt tatgtaacgg aacattcatt tattgtgcaa     480
actggtccgt ttaataaaaa tgtagtttta gagtgtgata taggcggaac aggagaaatc     540
tttctcaacg atggtcgggg gtactgggta gccatatcac aaattttaat ggaaaatgga     600
gttccaggca tccgatataa cccgaatccc tatactgctc atttcacagg tcaggcaag      660 ttgacaggca agatggggct tcaatctttt gtcaatgttg tagaacgtcc tttactaggt     720
cgtgcaggac aggttcgaga ataccaaatc ccagttacag aagaagcgg actagatat      780 cctatttttg atccagttat atctcgttag                                      810

<210> SEQ ID NO 4
<211> LENGTH: 269
<212> TYPE: PRT
<213> ORGANISM: Bacillus thuringiensis

<400> SEQUENCE: 4

Met Ala Ile Ile Asp Leu Leu Lys Glu Ile Lys Ile Trp Gly Glu Arg
1               5                   10                  15

Ala Ala Lys Gln His Asn Thr Thr Leu Lys Ser Ser Gly Tyr Leu Gly
            20                  25                  30

Arg Asp Pro Gly Asn Ile Tyr Asn Tyr Asn Met Lys Val Pro Asp Pro
        35                  40                  45

Ile Val Thr Asp Asn Pro Thr Asn Ser Ala Tyr Ala Lys Gly Thr Thr
```

```
                50                  55                  60
Pro Asn Pro Thr Ser Gln Pro Ile Val Arg Thr Ile Thr Phe Asn Glu
 65                  70                  75                  80

Thr Leu Thr Asp Ser Gln Ser Thr Thr Glu His Gly Ile Thr Ala
                 85                  90                  95

Gly Ala Ser Val Thr Val Lys Ser Glu Ala Gly Leu Leu Phe Ala Lys
                100                 105                 110

Val Gly Val Glu Ala Thr Val Ser Phe Glu Tyr Asn Tyr Thr Asn Ser
            115                 120                 125

Gln Thr Lys Thr Thr Glu Val Ser Arg Ser Trp Ser Asp Ser Leu Gln
        130                 135                 140

Ile Thr Val Pro Pro Gly Tyr Val Thr Glu His Ser Phe Ile Val Gln
145                 150                 155                 160

Thr Gly Pro Phe Asn Lys Asn Val Val Leu Glu Cys Asp Ile Gly Gly
                165                 170                 175

Thr Gly Glu Ile Phe Leu Asn Asp Gly Arg Gly Tyr Trp Val Ala Ile
            180                 185                 190

Ser Gln Ile Leu Met Glu Asn Gly Val Pro Gly Ile Arg Tyr Asn Pro
        195                 200                 205

Asn Pro Tyr Thr Ala His Phe Thr Gly Ser Gly Lys Leu Thr Gly Lys
    210                 215                 220

Met Gly Leu Gln Ser Phe Val Asn Val Val Glu Arg Pro Leu Leu Gly
225                 230                 235                 240

Arg Ala Gly Gln Val Arg Glu Tyr Gln Ile Pro Val Thr Gly Arg Ser
                245                 250                 255

Gly Leu Asp Ile Pro Ile Phe Asp Pro Val Ile Ser Arg
            260                 265

<210> SEQ ID NO 5
<211> LENGTH: 816
<212> TYPE: DNA
<213> ORGANISM: Bacillus thuringiensis

<400> SEQUENCE: 5
atggcgatta tagatctttt aaaagaaata gaagagtttg gtagagcttt tgcaccagga      60 accgggggg cttatgtttc ttcaggttat gagcctagta atccaggcag aatatataat     120
tacagaatgt ctataccaga tcctactgta actgataatc ctaccaatac agctgtggct    180
agaggaatta cgccaaatcg tacgactcag cctatagtca aactgttgg atatactgaa     240 accctgatgg attcccagtc tacaactaca gaacatggcg taacagccgg agccagtgtg    300
acagtgagta gtgaggcggg attgatattc gcaaaagtag gggttgaagc gacagttca    360 ttctcataca actatacaaa tacaaacacc tatacaacag aaacatctcg tagttggagt    420
gattcggtta caattacagt tcctccaggt tatcaaacgt cacatacatt tattgtgcaa    480
acaggacctt ttactaaaca ggcagtgtta aatgtgata acaggaac cgcatatgta    540 aatattaacg accgtatgc agggacttat agatggccga tagcacacgt tttagaatat     600
aagggaacgc taatactac aagggtgtct aatgatgtat ctcatttcac aggttcagga    660
acgttgacag gaaagatggg acttcaatcc tatgtcgata ttgtagaaac tcctttaacg    720
ggtcgtgccg acagactcg aagatatcaa attccactaa caggaagaag tgggcttaat    780
attcctattt ttgatccagt tgtgtctctt caatag                             816

<210> SEQ ID NO 6
```

<211> LENGTH: 271
<212> TYPE: PRT
<213> ORGANISM: Bacillus thuringiensis

<400> SEQUENCE: 6

Met Ala Ile Ile Asp Leu Leu Lys Glu Ile Glu Glu Phe Gly Arg Ala
1               5                   10                  15

Phe Ala Pro Gly Thr Gly Gly Ala Tyr Val Ser Ser Gly Tyr Glu Pro
            20                  25                  30

Ser Asn Pro Gly Arg Ile Tyr Asn Tyr Arg Met Ser Ile Pro Asp Pro
        35                  40                  45

Thr Val Thr Asp Asn Pro Thr Asn Thr Ala Val Ala Arg Gly Ile Thr
    50                  55                  60

Pro Asn Arg Thr Thr Gln Pro Ile Val Arg Thr Val Gly Tyr Thr Glu
65                  70                  75                  80

Thr Leu Met Asp Ser Gln Ser Thr Thr Glu His Gly Val Thr Ala
                85                  90                  95

Gly Ala Ser Val Thr Val Ser Ser Glu Ala Gly Leu Ile Phe Ala Lys
                100                 105                 110

Val Gly Val Glu Ala Thr Val Ser Phe Ser Tyr Asn Tyr Thr Asn Thr
            115                 120                 125

Asn Thr Tyr Thr Thr Glu Thr Ser Arg Ser Trp Ser Asp Ser Val Thr
        130                 135                 140

Ile Thr Val Pro Pro Gly Tyr Gln Thr Ser His Thr Phe Ile Val Gln
145                 150                 155                 160

Thr Gly Pro Phe Thr Lys Gln Ala Val Leu Glu Cys Asp Ile Thr Gly
                165                 170                 175

Thr Ala Tyr Val Asn Ile Asn Gly Pro Tyr Ala Gly Thr Tyr Arg Trp
            180                 185                 190

Pro Ile Ala His Val Leu Glu Tyr Lys Gly Thr Pro Asn Thr Thr Arg
        195                 200                 205

Val Ser Asn Asp Val Ser His Phe Thr Gly Ser Gly Thr Leu Thr Gly
    210                 215                 220

Lys Met Gly Leu Gln Ser Tyr Val Asp Ile Val Glu Thr Pro Leu Thr
225                 230                 235                 240

Gly Arg Ala Gly Gln Thr Arg Arg Tyr Gln Ile Pro Leu Thr Gly Arg
                245                 250                 255

Ser Gly Leu Asn Ile Pro Ile Phe Asp Pro Val Val Ser Leu Gln
            260                 265                 270

<210> SEQ ID NO 7
<211> LENGTH: 843
<212> TYPE: DNA
<213> ORGANISM: Bacillus thuringiensis

<400> SEQUENCE: 7
atggcgatta tagatcttaa acagattgcg gagacttttt ggagagattg gtgtaaaaag    60
ggtggcgttg actaccagag aacaataatg agtaattctg atggcagtaa tcctgttaga   120
atctataatt acaacatgtc tgtaccagat ccagttgtaa ttgataatcc cacaaattca   180
gctttagcta ggggatacac accaaatcct actagtcagc ctatagtcag aacaattaca   240
tttaatgaaa cacagtctga ctcacaatct acaacaacag aacatggcat aacagctggg   300
gtaagtgcga cagtaaaaag tgaggcggga tttgttttg caaaggtagg gtttgaagtg   360
acagtttcat ttgaatacaa ttacacgact tcaaacacat atacaacaga aacatcgcgt   420

-continued

```
agttgggagg attcgcttca atcacagtt ccgccaggtt atcaaacgac acacacattt    480
attgttcaaa ctgggccatt cgataaaaat gtagtgttag aatgtgatat aactggtacg    540
acaacctgtg tatataggta tcctggaaat tctgtggatc gtatgacagg atacaatggg    600
ggggtcattt cagaaatatt ggatatgcag ggtgttgcta atatcactta tccacaattc    660
ggcatcgctc atttcacagg ttcaggaaag ttgacaggca agatgggact tcaatcctat    720
gtcgatgttg tagaaactcc tttatcaggt cgtgcaggac agacgcgaaa atatcaaatt    780
ccattgacag gaagaagggg gctcgatatt cctattttg atccagtcgt atctcgtcag    840
tag                                                                  843
```

```
<210> SEQ ID NO 8
<211> LENGTH: 280
<212> TYPE: PRT
<213> ORGANISM: Bacillus thuringiensis

<400> SEQUENCE: 8

Met Ala Ile Ile Asp Leu Lys Gln Ile Ala Glu Thr Phe Trp Arg Asp
1               5                   10                  15

Trp Cys Lys Lys Gly Gly Val Asp Tyr Gln Arg Thr Ile Met Ser Asn
            20                  25                  30

Ser Asp Gly Ser Asn Pro Val Arg Ile Tyr Asn Tyr Asn Met Ser Val
        35                  40                  45

Pro Asp Pro Val Val Ile Asp Asn Pro Thr Asn Ser Ala Leu Ala Arg
    50                  55                  60

Gly Tyr Thr Pro Asn Pro Thr Ser Gln Pro Ile Val Arg Thr Ile Thr
65                  70                  75                  80

Phe Asn Glu Thr Gln Ser Asp Ser Gln Ser Thr Thr Glu His Gly
                85                  90                  95

Ile Thr Ala Gly Val Ser Ala Thr Val Lys Ser Glu Ala Gly Phe Val
            100                 105                 110

Phe Ala Lys Val Gly Phe Glu Val Thr Val Ser Phe Glu Tyr Asn Tyr
        115                 120                 125

Thr Thr Ser Asn Thr Tyr Thr Thr Glu Thr Ser Arg Ser Trp Glu Asp
    130                 135                 140

Ser Leu Gln Ile Thr Val Pro Pro Gly Tyr Gln Thr Thr His Thr Phe
145                 150                 155                 160

Ile Val Gln Thr Gly Pro Phe Asp Lys Asn Val Val Leu Glu Cys Asp
                165                 170                 175

Ile Thr Gly Thr Thr Thr Cys Val Tyr Arg Tyr Pro Gly Asn Ser Val
            180                 185                 190

Asp Arg Met Thr Gly Tyr Asn Gly Gly Val Ile Ser Glu Ile Leu Asp
        195                 200                 205

Met Gln Gly Val Ala Asn Ile Thr Tyr Pro Gln Phe Gly Ile Ala His
    210                 215                 220

Phe Thr Gly Ser Gly Lys Leu Thr Gly Lys Met Gly Leu Gln Ser Tyr
225                 230                 235                 240

Val Asp Val Val Glu Thr Pro Leu Ser Gly Arg Ala Gly Gln Thr Arg
                245                 250                 255

Lys Tyr Gln Ile Pro Leu Thr Gly Arg Arg Gly Leu Asp Ile Pro Ile
            260                 265                 270

Phe Asp Pro Val Val Ser Arg Gln
        275                 280
```

```
<210> SEQ ID NO 9
<211> LENGTH: 822
<212> TYPE: DNA
<213> ORGANISM: Bacillus thuringiensis

<400> SEQUENCE: 9
atggctattt tagatcttaa aaagttaaca gaggattatt ggcgagattt ttgtataaag      60
aataaatatg aatttgtgaa cgcagaaatg agttggctga acggccagta tcctgttcga     120
ctatataatt taaacgtgca ggtaccagat cctattgtga ctgataatcc cacaaattca     180
gctgtggcta ggggagtcac gcctaatcct actagccagc ctatagtcag aactgttgga     240
tatactgaaa ccctgacaga ttcccaatct acaacaacag acatggcgt aacagctggg      300 gcaagtgtga cagtaaaaag tgaggcggga tttctctttg caaggtagg tgtggaggct      360 acggtttcat tgaatacaa ttacacgact tcaaaaacat atacgacaga atatctcgt       420 agttggactg attcagttac aatcacagtt ccgccaggtt accaaacgac acatacattt     480
attgttcaaa ctgggccgtt tgataaaaat gttgttttag agtgtgatat agatggttac     540
acaatgtgtt actacaggga gaatggtata acaaaatatg ttaaccacag tatggcaaga     600
attttgcatg aaatgggcta cacagattct acacacatat atgtcgctca tttcataggt     660
tcaggaaagt tggaaggtaa gatgggactt caatcctatg tcaatgttgt agaaactcct     720
ttaccaggtc gtgcaggaca gacgcgagaa tatcaaattc cagttacaag aagaagtggt     780
ctcgatattc ctattttga tcccatagta tctcgtcagt ag                         822

<210> SEQ ID NO 10
<211> LENGTH: 273
<212> TYPE: PRT
<213> ORGANISM: Bacillus thuringiensis

<400> SEQUENCE: 10

Met Ala Ile Leu Asp Leu Lys Lys Leu Thr Glu Asp Tyr Trp Arg Asp
1               5                   10                  15

Phe Cys Ile Lys Asn Lys Tyr Glu Phe Val Asn Ala Glu Met Ser Trp
            20                  25                  30

Leu Asn Gly Gln Tyr Pro Val Arg Leu Tyr Asn Leu Asn Val Gln Val
        35                  40                  45

Pro Asp Pro Ile Val Thr Asp Asn Pro Thr Asn Ser Ala Val Ala Arg
    50                  55                  60

Gly Val Thr Pro Asn Pro Thr Ser Gln Pro Ile Val Arg Thr Val Gly
65                  70                  75                  80

Tyr Thr Glu Thr Leu Thr Asp Ser Gln Ser Thr Thr Thr Glu His Gly
                85                  90                  95

Val Thr Ala Gly Ala Ser Val Thr Val Lys Ser Glu Ala Gly Phe Leu
            100                 105                 110

Phe Ala Lys Val Gly Val Glu Ala Thr Val Ser Phe Glu Tyr Asn Tyr
        115                 120                 125

Thr Thr Ser Lys Thr Tyr Thr Thr Glu Ile Ser Arg Ser Trp Thr Asp
    130                 135                 140

Ser Val Thr Ile Thr Val Pro Pro Gly Tyr Gln Thr Thr His Thr Phe
145                 150                 155                 160

Ile Val Gln Thr Gly Pro Phe Asp Lys Asn Val Val Leu Glu Cys Asp
                165                 170                 175

Ile Asp Gly Tyr Thr Met Cys Tyr Tyr Arg Glu Asn Gly Ile Thr Lys
            180                 185                 190
```

Tyr Val Asn His Ser Met Ala Arg Ile Leu His Glu Met Gly Tyr Thr
            195                 200                 205

Asp Ser Thr His Ile Tyr Val Ala His Phe Ile Gly Ser Gly Lys Leu
        210                 215                 220

Glu Gly Lys Met Gly Leu Gln Ser Tyr Val Asn Val Val Glu Thr Pro
225                 230                 235                 240

Leu Pro Gly Arg Ala Gly Gln Thr Arg Glu Tyr Gln Ile Pro Val Thr
                245                 250                 255

Arg Arg Ser Gly Leu Asp Ile Pro Ile Phe Asp Pro Ile Val Ser Arg
            260                 265                 270

Gln

<210> SEQ ID NO 11
<211> LENGTH: 852
<212> TYPE: DNA
<213> ORGANISM: Bacillus thuringiensis

<400> SEQUENCE: 11
atggcgattt tagatcttca cacggtagca gcgaattatt ggaaagagta ttgtcggagg      60
gctggtttta tctatcaaag ctcaacactg accggcaaac ccggcacaga attttacgaa     120
aagcttggcc ccactagaat atataattat aaaatgtctg taccagatcc tatcgtgtct     180
gataatccca aaatgcagc tttggctaag ggatatacac aaaccctac ttcgcagcca      240 gtagttagaa caattacttt taccgaaaca attgctgatt cccagtctac aacaacagaa     300
catggtgtaa ccgctggggc aagtgtgaca gtaaaaagtg aagcgggatt ccttttttgcg    360 aaagtaggtg tggaggccac gatttcattt gaatacaatt atacgaattc acagacaaaa    420
acgacagaaa catctcggag ttggcaggat tcacttcaaa tcacagttcc tccaggttat     480
caaacggaac atacatttat tgtgcaaact ggtccattcg ataaacaggt agtattagaa    540
tgtgatatag caggtgcaac aacttgttat tactttaacc aaaagctgg tgtgaatgac    600 tctacgtacg aacccatagt attcgcgctt gagggtattc ctggtatttc aaatgttgag    660
tacaacaatt acactgccca tttcacaggg gcaggaaggt taacaggcaa gatgggactt    720
caatcttttg tagatcttgt agaacgccct ttagcaggtc gtgcaggaca gactcgaaga    780
tatcaaattc cgcttacagg aaaaagcggg ctcgatattc ctattttga tcgagtcgta   840 tctcgtcagt ag                                                         852

<210> SEQ ID NO 12
<211> LENGTH: 283
<212> TYPE: PRT
<213> ORGANISM: Bacillus thuringiensis

<400> SEQUENCE: 12

Met Ala Ile Leu Asp Leu His Thr Val Ala Ala Asn Tyr Trp Lys Glu
1                5                  10                  15

Tyr Cys Arg Arg Ala Gly Phe Ile Tyr Gln Ser Ser Thr Leu Thr Gly
            20                  25                  30

Lys Pro Gly Thr Glu Phe Tyr Glu Lys Leu Gly Pro Thr Arg Ile Tyr
        35                  40                  45

Asn Tyr Lys Met Ser Val Pro Asp Pro Ile Val Ser Asp Asn Pro Thr
    50                  55                  60

Asn Ala Ala Leu Ala Lys Gly Tyr Thr Pro Asn Pro Thr Ser Gln Pro
65                  70                  75                  80

Val Val Arg Thr Ile Thr Phe Thr Glu Thr Ile Ala Asp Ser Gln Ser 85                  90                  95
Thr Thr Thr Glu His Gly Val Thr Ala Gly Ala Ser Val Thr Val Lys
                100                 105                 110
Ser Glu Ala Gly Phe Leu Phe Ala Lys Val Gly Val Glu Ala Thr Ile
            115                 120                 125
Ser Phe Glu Tyr Asn Tyr Thr Asn Ser Gln Thr Lys Thr Thr Glu Thr
        130                 135                 140
Ser Arg Ser Trp Gln Asp Ser Leu Gln Ile Thr Val Pro Pro Gly Tyr
145                 150                 155                 160
Gln Thr Glu His Thr Phe Ile Val Gln Thr Gly Pro Phe Asp Lys Gln
                165                 170                 175
Val Val Leu Glu Cys Asp Ile Ala Gly Ala Thr Thr Cys Tyr Tyr Phe
                180                 185                 190
Asn Pro Lys Ala Gly Val Asn Asp Ser Thr Tyr Glu Pro Ile Val Phe
            195                 200                 205
Ala Leu Glu Gly Ile Pro Gly Ile Ser Asn Val Glu Tyr Asn Asn Tyr
        210                 215                 220
Thr Ala His Phe Thr Gly Ala Gly Arg Leu Thr Gly Lys Met Gly Leu
225                 230                 235                 240
Gln Ser Phe Val Asp Leu Val Glu Arg Pro Leu Ala Gly Arg Ala Gly
                245                 250                 255
Gln Thr Arg Arg Tyr Gln Ile Pro Leu Thr Gly Lys Ser Gly Leu Asp
                260                 265                 270
Ile Pro Ile Phe Asp Arg Val Val Ser Arg Gln
            275                 280

<210> SEQ ID NO 13
<211> LENGTH: 822
<212> TYPE: DNA
<213> ORGANISM: Bacillus thuringiensis

<400> SEQUENCE: 13
atggcaattt tagatcttag agcggttgcg gagaattact ggaagaaata ttgtgcatcg      60
aaaggttata attatataag gacagatatg cccgatgtag aaatctctaa tttcaatata     120
aatatattag atcctgtggt atttgcaaat cctgggaata cagctcttgc ttttggaact     180
acaccaaacc gtacttcccg ggacttactt agaactctta cattcaacga acacagact     240
gattcacagt ctaccacaac ggaacacggc ataacagcag ggtatagtgt aacagcaaga     300
gctgaggcaa gtatactatt tgcgacagta ggcatagaaa ctacaatgag tttggaatac     360
aattatacaa attcaaaaac atatacgaaa gaagtatctc gtagttggga ggattctatt     420
acaatcacag ttcctccagg ttatgaaaca cgccatacat ttatagtaca acgggtcca     480
tttaataaaa atgtagcgtt agagtgtgat ataacaggtt aacaacctg ctggttcagt      540
catccgcagg tgccgggta  ccctttgga  gaatctgact  atatgtcaag  gatattagat    600
tacgaaggta ttcctaatat atctcttata ggttcaaata tatcgctcg tttcaaaggt     660
gtaggaaatt tggtcggaag tatggcactt caatcttata ttgatctcga gaacgtcct     720
ttaccaggtc gttccggaca gactcgaaga tatcaaattc cggttactgg cagaagcggc     780
atcgatattc ctattttgga tccagtccta tctcgtcaat ag                       822

<210> SEQ ID NO 14
<211> LENGTH: 273
<212> TYPE: PRT
<213> ORGANISM: Bacillus thuringiensis

<400> SEQUENCE: 14

```
Met Ala Ile Leu Asp Leu Arg Ala Val Ala Glu Asn Tyr Trp Lys Lys
1               5                   10                  15

Tyr Cys Ala Ser Lys Gly Tyr Asn Tyr Ile Arg Thr Asp Met Pro Asp
            20                  25                  30

Val Glu Ile Ser Asn Phe Asn Ile Asn Ile Leu Asp Pro Val Val Phe
        35                  40                  45

Ala Asn Pro Gly Asn Thr Ala Leu Ala Phe Gly Thr Thr Pro Asn Arg
    50                  55                  60

Thr Ser Arg Asp Leu Leu Arg Thr Leu Thr Phe Asn Glu Thr Gln Thr
65                  70                  75                  80

Asp Ser Gln Ser Thr Thr Thr Glu His Gly Ile Thr Ala Gly Tyr Ser
                85                  90                  95

Val Thr Ala Arg Ala Glu Ala Ser Ile Leu Phe Ala Thr Val Gly Ile
                100                 105                 110

Glu Thr Thr Met Ser Leu Glu Tyr Asn Tyr Thr Asn Ser Lys Thr Tyr
            115                 120                 125

Thr Lys Glu Val Ser Arg Ser Trp Glu Asp Ser Ile Thr Ile Thr Val
130                 135                 140

Pro Pro Gly Tyr Glu Thr Arg His Thr Phe Ile Val Gln Thr Gly Pro
145                 150                 155                 160

Phe Asn Lys Asn Val Ala Leu Glu Cys Asp Ile Thr Gly Leu Thr Thr
                165                 170                 175

Cys Trp Phe Ser His Pro Gln Val Pro Gly Tyr Thr Phe Gly Glu Ser
            180                 185                 190

Asp Tyr Met Ser Arg Ile Leu Asp Tyr Glu Gly Ile Pro Asn Ile Ser
        195                 200                 205

Leu Ile Gly Ser Asn Asn Ile Ala Arg Phe Lys Gly Val Gly Asn Leu
    210                 215                 220

Val Gly Ser Met Ala Leu Gln Ser Tyr Ile Asp Leu Glu Glu Arg Pro
225                 230                 235                 240

Leu Pro Gly Arg Ser Gly Gln Thr Arg Arg Tyr Gln Ile Pro Val Thr
                245                 250                 255

Gly Arg Ser Gly Ile Asp Ile Pro Ile Leu Asp Pro Val Leu Ser Arg
            260                 265                 270

Gln
```

<210> SEQ ID NO 15
<211> LENGTH: 825
<212> TYPE: DNA
<213> ORGANISM: Bacillus thuringiensis

<400> SEQUENCE: 15

```
atggcgatta taaatcttgc gaatgagttg gcaatttggg caaagaggtg gtgtgctgca      60
agggGatAca catatttagt aagtggtctc caggctcata ctggtaatta tggtagaata     120
tacaattaca atatgtctgt accagatcct attgtaactg ataatcctac aaatgcagct     180
atggctaggg gaactacgcc aaatccaact agtcagccta atcagaac gatttcattt       240 aatgaaactc ttactgattc gcagtctaca gcaacagaac acggaataac ggctggagca     300
gaagtaacag taaaaagtga agcaggatta attttgcaa aggtaggttt tgaagttaag      360
gtttcatttc aatacaatta cacgactaca aacacatata cgacagaaac gtctcggagt     420
tggacggatt cgcttcaaat caccgttccg ccaggttatg taacggagca tacatttatt     480
```
gtgcaaactg gtccatatag taaaaatgta gtattagaag ctgacatagc agggcatgga 540
tggtttaatt atagtgctcc tggttacact ggtactggaa tagttaatat cacgcaagta 600
ttatatgaca ataaagttcc aggcgttacc ccctacccag acaatttcta tgctcgtttc 660
agaggttcag gaaagttaga aggaaaaatg ggacttcaat cttttgtcaa tcttgtagaa 720
agacctttac taggtcgtgc agggcaggtt cgggaatatc aaattccagt ttcgctacca 780
agcggattag atattcctat ttttgaccct gtggtatctc ttcag 825

<210> SEQ ID NO 16
<211> LENGTH: 275
<212> TYPE: PRT
<213> ORGANISM: Bacillus thuringiensis

<400> SEQUENCE: 16

Met Ala Ile Ile Asn Leu Ala Asn Glu Leu Ala Ile Trp Ala Lys Arg
1 5 10 15

Trp Cys Ala Ala Arg Gly Tyr Thr Tyr Leu Val Ser Gly Leu Gln Ala
20 25 30

His Thr Gly Asn Tyr Gly Arg Ile Tyr Asn Tyr Asn Met Ser Val Pro
35 40 45

Asp Pro Ile Val Thr Asp Asn Pro Thr Asn Ala Ala Met Ala Arg Gly
50 55 60

Thr Thr Pro Asn Pro Thr Ser Gln Pro Ile Ile Arg Thr Ile Ser Phe
65 70 75 80

Asn Glu Thr Leu Thr Asp Ser Gln Ser Thr Ala Thr Glu His Gly Ile
85 90 95

Thr Ala Gly Ala Glu Val Thr Val Lys Ser Glu Ala Gly Leu Ile Phe
100 105 110

Ala Lys Val Gly Phe Glu Val Lys Val Ser Phe Gln Tyr Asn Tyr Thr
115 120 125

Thr Thr Asn Thr Tyr Thr Thr Glu Thr Ser Arg Ser Trp Thr Asp Ser
130 135 140

Leu Gln Ile Thr Val Pro Pro Gly Tyr Val Thr Glu His Thr Phe Ile
145 150 155 160

Val Gln Thr Gly Pro Tyr Ser Lys Asn Val Val Leu Glu Ala Asp Ile
165 170 175

Ala Gly His Gly Trp Phe Asn Tyr Ser Ala Pro Gly Tyr Thr Gly Thr
180 185 190

Gly Ile Val Asn Ile Thr Gln Val Leu Tyr Asp Asn Lys Val Pro Gly
195 200 205

Val Thr Pro Tyr Pro Asp Asn Phe Tyr Ala Arg Phe Arg Gly Ser Gly
210 215 220

Lys Leu Glu Gly Lys Met Gly Leu Gln Ser Phe Val Asn Leu Val Glu
225 230 235 240

Arg Pro Leu Leu Gly Arg Ala Gly Gln Val Arg Glu Tyr Gln Ile Pro
245 250 255

Val Ser Leu Pro Ser Gly Leu Asp Ile Pro Ile Phe Asp Pro Val Val
260 265 270

Ser Leu Gln
275

<210> SEQ ID NO 17
<211> LENGTH: 834
<212> TYPE: DNA

<213> ORGANISM: Bacillus thuringiensis

<400> SEQUENCE: 17

```
gtggatcata tggcgattat caatctcgcg aatgagttgg caatttgggc aaagaggtgg      60
tgtgctgaaa agggatacac atatgaatca gtggcctac aggctcatac tggtaattat     120
ggtagaatat acaattataa tatatctgta ccagaccta ttgtaactga taatcctaca     180
aatacagcta tggcgagggg aaccacgcca aattcaacta gtcagcctat agtcagaacg     240
attacattta tgaaacgct tactgattca cagtctacaa caacagaaca tggtatcaca     300
gctggagtaa gtgcgacagt aaaaagtgaa gcgggatttg tttttgcaaa ggtaggtttt     360
gaagttacgg tttcatttca atacaattac acgactacaa acacatatac gacagaaacg     420
tctcggagtt ggacagattc gcttcaagtc accgttccgc caggttatgt aacgaaacat     480
acatttattg tgcaaactgg tccatatagt aaaaatgtag tattagaggc tgacatagca     540
ggacatggat ggtttaatta tagggctcct ggttatactg ctactggaat agttaatatc     600
acacgagtat tatatgacaa taaggttcca ggcattactc cctatccaga cgatttctat     660
gctcgattca gaggttcagg aaagttagaa ggaaaaatgg gacttcaatc ttttgtaaat     720
attgtagaaa gacctttatc aggtcgtgca gggcaggttc gagaatatca aattccagtt     780
tcgctacaaa gtggattagg aatccctatc tttgatccag ttgtatctct tcag           834
```

<210> SEQ ID NO 18
<211> LENGTH: 278
<212> TYPE: PRT
<213> ORGANISM: Bacillus thuringiensis

<400> SEQUENCE: 18

```
Met Asp His Met Ala Ile Ile Asn Leu Ala Asn Glu Leu Ala Ile Trp
  1               5                  10                  15
Ala Lys Arg Trp Cys Ala Glu Lys Gly Tyr Thr Tyr Glu Ser Ser Gly
             20                  25                  30
Leu Gln Ala His Thr Gly Asn Tyr Gly Arg Ile Tyr Asn Tyr Asn Ile
         35                  40                  45
Ser Val Pro Asp Pro Ile Val Thr Asp Asn Pro Thr Asn Thr Ala Met
     50                  55                  60
Ala Arg Gly Thr Thr Pro Asn Ser Thr Ser Gln Pro Ile Val Arg Thr
 65                  70                  75                  80
Ile Thr Phe Asn Glu Thr Leu Thr Asp Ser Gln Ser Thr Thr Thr Glu
                 85                  90                  95
His Gly Ile Thr Ala Gly Val Ser Ala Thr Val Lys Ser Glu Ala Gly
            100                 105                 110
Phe Val Phe Ala Lys Val Gly Phe Glu Val Thr Val Ser Phe Gln Tyr
        115                 120                 125
Asn Tyr Thr Thr Thr Asn Thr Tyr Thr Thr Glu Thr Ser Arg Ser Trp
    130                 135                 140
Thr Asp Ser Leu Gln Val Thr Val Pro Pro Gly Tyr Val Thr Glu His
145                 150                 155                 160
Thr Phe Ile Val Gln Thr Gly Pro Tyr Ser Lys Asn Val Val Leu Glu
                165                 170                 175
Ala Asp Ile Ala Gly His Gly Trp Phe Asn Tyr Arg Ala Pro Gly Tyr
            180                 185                 190
Thr Ala Thr Gly Ile Val Asn Ile Thr Arg Val Leu Tyr Asp Asn Lys
        195                 200                 205
```

```
Val Pro Gly Ile Thr Pro Tyr Pro Asp Asp Phe Tyr Ala Arg Phe Arg
    210                 215                 220
Gly Ser Gly Lys Leu Glu Gly Lys Met Gly Leu Gln Ser Phe Val Asn
225                 230                 235                 240
Ile Val Glu Arg Pro Leu Ser Gly Arg Ala Gly Gln Val Arg Glu Tyr
                245                 250                 255
Gln Ile Pro Val Ser Leu Gln Ser Gly Leu Gly Ile Pro Ile Phe Asp
            260                 265                 270
Pro Val Val Ser Leu Gln
        275
```

<210> SEQ ID NO 19
<211> LENGTH: 810
<212> TYPE: DNA
<213> ORGANISM: Artificial Sequence
<220> FEATURE:
<223> OTHER INFORMATION: modified nucleotide sequence designed for use
      in plants
<220> FEATURE:
<221> NAME/KEY: misc_feature
<222> LOCATION: (1)..(810)
<223> OTHER INFORMATION: codon modified coding sequence
<220> FEATURE:
<221> NAME/KEY: misc_feature
<222> LOCATION: (1)..(810)
<223> OTHER INFORMATION: modified nucleotide sequence designed for use
      in plants

<400> SEQUENCE: 19

```
atggctatca tcaacctcct gaacgaaatc cgcatctggg agaacgtgc  cgcgcgcgac    60
cggaacacga cccttaaatc ctccggctac ctcgcgtcca gtcctggccg  catctacaac   120
tacaacatga gcgtgccgga cccagtggtc actgacaatc ccaccaacgc  agcactcgcc   180
cgtggaacga cgcccaaccc tactactcag cccatcgtgc ggaccatcac  cttcaacgag   240
accctgaccg acagtcagtc caccaccacg gagcacggca ttacagccgg  tgtctccgcc   300
accgtcaagt cagaggcggg cttcgtattc gctaaggtcg gattcgaggt  cacagtgtca   360
ttccagtaca actacactac tagcaacact tacaccaccg agacttcaag  atcctggacc   420
gactcgttgc agatcaccgt cccgccaggc tacgtgaccg aacacacctt  catcgtgcag   480
acgggaccat tctccaagaa cgtcgtcctg gagtgcgaca tcgacggtta  cgctcagatc   540
tggttcgcta atggcagcgg catcaccctc ggcgtaagcc aagtgttact  ggagaatagc   600
gtgcctggaa tcagatggct gggcgggtac gtcactcgct tcacgggctc  cggcaagctg   660
accgggaaga tgggcttgca gtccttcgtc aatgtggtcg aacgcccgtt  gtcgggtcgg   720
gctgggcaag ttcgagagta ccagatccct gtcacgggcc ggtccggcct  cgacatccca   780
atcttcgatt ccatcgtgtc tcgccagtga                                    810
```

<210> SEQ ID NO 20
<211> LENGTH: 810
<212> TYPE: DNA
<213> ORGANISM: Artificial Sequence
<220> FEATURE:
<223> OTHER INFORMATION: modified nucleotide sequence designed for use
      in plants
<220> FEATURE:
<221> NAME/KEY: misc_feature
<222> LOCATION: (1)..(810)
<223> OTHER INFORMATION: codon modified coding sequence
<220> FEATURE:
<221> NAME/KEY: misc_feature
<222> LOCATION: (1)..(810)
<223> OTHER INFORMATION: modified nucleotide sequence designed for use in plants

<400> SEQUENCE: 20

```
atggcgatca tcgacctcct caaggagatc aagatctggg gcgaacgggc ggccaagcag      60
cataacacca cgctcaagtc gtcgggctat ctcggtcgtg accctgggaa catctacaac     120
tacaacatga aggtgcctga ccctattgtg actgataacc cgaccaactc agcctacgcg     180
aagggcacca cacccaaccc gaccagccag ccaattgtac ggaccatcac cttcaacgag     240
accctcaccg actcccaatc cacgacgacg gagcatggca tcactgcggg agccagcgtc     300
acagtcaagt ccgaggctgg cctgctattc gcaaaggtcg gcgttgaggc cactgtgagc     360
ttcgagtaca actacaccaa tagccagacc aagaccacgg aggtgtcccg tagttggtcc     420
gatagcctcc agatcacggt gccaccaggc tacgtgaccg agcattcctt catcgtccag     480
accgggcctt caacaagaa cgtggtgctg aatgcgaca tcggcgggac cggcgagatc     540
ttcctgaacg atggccgtgg ctactgggtt gcgattagcc agatcctgat ggagaatggt     600
gtacctggaa tccgttacaa tccgaatccg tacacagccc actttactgg gtctggcaaa     660
ctaaccggaa agatgggcct ccagagcttc gtgaacgtgg tcgaacgccc gctgcttggg     720
cgggctggtc aagtgcggga gtaccagata ccggtgaccg ggcgctccgg tctcgacatc     780
cctatcttcg atcctgtgat tagccggtga                                      810
```

<210> SEQ ID NO 21
<211> LENGTH: 816
<212> TYPE: DNA
<213> ORGANISM: Artificial Sequence
<220> FEATURE:
<223> OTHER INFORMATION: modified nucleotide sequence designed for use
      in plants
<220> FEATURE:
<221> NAME/KEY: misc_feature
<222> LOCATION: (1)..(816)
<223> OTHER INFORMATION: codon modified coding sequence
<220> FEATURE:
<221> NAME/KEY: misc_feature
<222> LOCATION: (1)..(816)
<223> OTHER INFORMATION: modified nucleotide sequence designed for use
      in plants

<400> SEQUENCE: 21

```
atggctatca tcgacctcct caaggagatt gaggagttcg ggcgcgcttt cgcgccagga      60
accggcggcg cgtacgtctc gtcaggctac gagccttcga acccaggcg gatctacaac     120 taccgtatgt ccatcccgga ccctaccgtg accgacaatc ctaccaacac cgccgtagcg     180
cgtggtatca cacccaacag gacgacccag cccattgtcc ggaccgttgg ctacaccgag     240
accctcatgg actcgcagag taccacgaca gagcatggcg taacggctgg cgcttcagtt     300
acggtgtcga gcgaagctgg gctcatcttc gccaaagtgg gcgtggaggc aaccgtgtcg     360
ttctcgtaca actacaccaa taccaacacc tacacaaccg aaacgagccg gtcgtggtcg     420
gactccgtga cgattacggt gccacccggt taccaaactt cccacacctt cattgtgcaa     480
actggaccct tcacgaaaca agcagtgctg aatgcgaca ttacgggcac cgcttacgtg     540
aacattaacg gcccatacgc gggcacctac cgttggccca tcgcgcacgt gctggagtac     600
aagggcactc caaacaccac acgggtctcc aatgacgttt cacactttac cggatcgggc     660
acgctaaccg gaaagatggg tctgcaaagt tacgtggaca tcgtagagac tcctctgaca     720
```

-continued

```
ggcagagcgg gccagacccg gcgctatcag ataccgctta cgggacggtc cggacttaac    780
atcccgatct tcgacccagt ggtcagcctc cagtga                              816
```

PESTICIDAL TOXIN ACTIVE AGAINST COLEOPTERAN AND/OR HEMIPTERAN INSECTS

CROSS REFERENCE TO RELATED APPLICATIONS

This application claims priority to U.S. Provisional Application Ser. No. 61/864,045 filed Aug. 9, 2013, which is incorporated herein by reference in its entirety.

INCORPORATION OF SEQUENCE LISTING

A computer readable form of the Sequence Listing is provided herein, containing the file named "38_21_59639_0001_SEQUENCE_LISTING_ST25.txt", which is 37,301 bytes in size (measured in operating system MS-Windows) and was created on Jun. 13, 2014, is contemporaneously filed by electronic submission (using the United States Patent Office EFS-Web filing system) and is incorporated herein by reference in its entirety.

FIELD OF THE INVENTION

The invention generally relates to the field of insect inhibitory proteins. In particular, the present invention relates to proteins exhibiting insect inhibitory activity against agricultural relevant pests of crop plants and seeds, particularly Coleopteran and Hemipteran species of insect pests.

BACKGROUND OF THE INVENTION

Insect inhibitory proteins derived from *Bacillus thuringiensis* (Bt) are known in the art. These proteins can be used to control agricultural pests of crop plants by spraying formulations containing these proteins onto plants/seeds or by expressing these proteins in plants/seeds.

Only a few Bt proteins have been developed for use as transgenic traits for commercial use by farmers to control insect pests. Farmers rely on these proteins to provide a prescribed spectrum of pest control, and may continue to rely on broad spectrum chemistries in foliar and soil applications to control unprescribed pests. Certain Coleopteran insects such as Western corn rootworm (WCR, *Diabrotica virgifera virgifera*) and Southern corn rootworm (SCR, *Diabrotica undecimpunctata*) species, as well as Hemipteran species such as *Lygus lineolaris* (TPB) and *Lygus hesperus* (WTBP) have been shown to be particularly refractory to such transgenic traits. Hence, there is a need for insect inhibitory proteins that exhibit activity against a broader spectrum of insect pest species.

Here, a novel protein family has been disclosed and exemplary recombinant proteins exhibiting insecticidal activity against Coleoptera and Hemiptera are described.

SUMMARY OF THE INVENTION

Disclosed herein is a novel group of insect inhibitory polypeptides (toxin proteins) which are shown to exhibit inhibitory activity against one or more pests of crop plants. Each of the proteins can be used alone or in combination with each other and with other Bt proteins and toxic agents in formulations and in planta, thus providing alternatives to Bt proteins and insecticide chemistries currently in use in agricultural systems.

Recombinant polypeptides are provided which exhibit inhibitory activity against Coleopteran and/or Hemipteran pest species and which exhibit optionally
(a) at least 75.5% amino acid identity to SEQ ID NO:2;
(b) at least 70% amino acid identity to SEQ ID NO:4; or
(c) at least 62% amino acid identity to SEQ ID NO:6.

Insect inhibitory compositions are provided comprising the aforementioned recombinant polypeptides along with methods for controlling Coleopteran and/or Hemipteran species using such recombinant polypeptides.

DNA constructs are provided comprising a polynucleotide operably linked to a heterologous promoter, which polynucleotide encodes an insecticidal polypeptide or insecticidal fragment thereof active against a Coleopteran and/or Hemipteran species pest. The insecticidal polypeptide comprises an amino acid sequence exhibiting
(a) at least 76% amino acid identity to SEQ ID NO:2 (TIC3131);
(b) at least 70% amino acid identity to SEQ ID NO:4 (TIC3400); or
(c) at least 62% amino acid identity to SEQ ID NO:6 (TIC3407).

Transgenic plant cells, plants, or plant parts comprising the DNA constructs and methods of controlling a Coleopteran and/or Hemipteran species pest using such transgenic plant cells, plants or plant parts are also provided.

Recombinant microorganisms comprising the DNA constructs are also provided. Such microorganism includes, but is not limited to, a bacterium, a plant cell, and a fungal cell. The bacterium may be a *Bacillus* species, an *Escherischia* species, a *Rhizobium* species, an *Agrobacterium* species, and a *Pseudomonas* species. The plant cell includes, but is not limited to, a corn (maize) plant cell, a cotton (gossypium) plant cell, a soybean (brassica) plant cell, a sugarcane plant cell, a canola (mustard) plant cell, a rize (oryza) plant cell, and a vegetable plant cell.

Commodity products produced from the plant cell, plant or plant part of the present invention or processed plant products are provided that comprise a detectable amount of the DNA constructs. Such processed products include, but are not limited to, plant biomass, oil, meal, animal feed, flour, flakes, bran, lint, hulls, and processed seed.

Methods of making transgenic plants are also provided. Such methods include introducing the DNA construct into a plant cell and selecting a transgenic plant that expresses an insect inhibitory amount of the recombinant polypeptide encoded by the DNA construct.

Other embodiments, features, and advantages of the invention will be apparent from the following detailed description, examples, and claims.

BRIEF DESCRIPTION OF THE SEQUENCES

SEQ ID NO:1 is a nucleotide sequence encoding a TIC3131 protein.
SEQ ID NO:2 is an amino acid sequence of a TIC3131 protein toxin.
SEQ ID NO:3 is a nucleotide sequence encoding a TIC3400 protein.
SEQ ID NO:4 is an amino acid sequence of a TIC3400 protein toxin.
SEQ ID NO:5 is a nucleotide sequence encoding a TIC3407 protein.
SEQ ID NO:6 is an amino acid sequence of a TIC3407 protein toxin.
SEQ ID NO:7 is a nucleotide sequence encoding a TIC2807 protein.

SEQ ID NO:8 is an amino acid sequence of a TIC2807 protein toxin.

SEQ ID NO:9 is a nucleotide sequence encoding a TIC2808 protein.

SEQ ID NO:10 is an amino acid sequence of a TIC2808 protein toxin.

SEQ ID NO:11 is a nucleotide sequence encoding a TIC3093 protein.

SEQ ID NO:12 is an amino acid sequence of a TIC3093 protein toxin.

SEQ ID NO:13 is a nucleotide sequence encoding a TIC2019 protein.

SEQ ID NO:14 is an amino acid sequence of a TIC2019 protein toxin.

SEQ ID NO:15 is a nucleotide sequence encoding Cry45Aa1 protein.

SEQ ID NO:16 is an amino acid sequence of Cry45Aa1 protein toxin.

SEQ ID NO:17 is a nucleotide sequence encoding AXMI108 protein.

SEQ ID NO:18 is an amino acid sequence of AXMI108 protein toxin.

SEQ ID NO:19 is a modified nucleotide sequence designed for use in plants and encoding a TIC3131 protein.

SEQ ID NO:20 is a modified nucleotide sequence designed for use in plants and encoding a TIC3400 protein.

SEQ ID NO:21 is a modified nucleotide sequence designed for use in plants and encoding a TIC3407 protein.

DETAILED DESCRIPTION OF THE INVENTION

In order to avoid the development of, or circumvent insect resistance against currently used proteins, new proteins with different modes of action (MOA) as well as a broad spectrum and efficacy are needed for Coleopteran and/or Hemipteran insect control. Certain Hemiptera species, particularly *Lygus* bugs, are common pest of crop plants, and typically are only controlled using broad spectrum chemistries, e.g., endosulfan, acephate, and oxamyl, which can persist in and harm the environment. A few Bt proteins have been developed in formulations or as transgenic traits for commercial use by farmers to control Coleopteran and Lepidopteran pest species, but no Bt proteins have been used for commercial control of Hemipteran pest species. One way to address this need for Coleopteran and/or Hemipteran inhibitory proteins is to sequence Bt genomes in hopes to discover new insecticidal proteins.

Bt strain genomes were sequenced and proteins were discovered that exhibit activity against *Diabrotica* species (Western Corn Rootworms (WCR) and Southern Corn Rootworms (SCR)), Colorado potato beetles (CPB), Western Tarnished Plant Bugs (WTPB) and Tarnished Plant Bugs (TPB). These proteins were cloned into host strains and expressed for subsequent bioassay testing against Coleopteran and/or Hemipteran pest species. It was shown that these proteins exhibited commercial levels of bioactivity against these insect species. For example, TIC31.31, TIC3400 and TIC3407 exhibit activity against CPB; TIC3131, TIC3400 and TIC3407 exhibit activity against WCR; and TIC3131 exhibits activity against SCR. It was also shown that TIC3131 and TIC3400 exhibit activity against WTPB and TPB.

Also disclosed herein are nucleotide sequences that encode insecticidal proteins identified herein as TIC3131, TIC3400 and TIC3407, which when compared to known proteins having Hemipteran or Coleopteran activity, have alternative MOA's and activity against a broader spectrum of insect pests and can delay or avoid development of resistance.

Artificial nucleotide sequences were designed that encode each of the toxin proteins TIC3131 TIC3400 and TIC3407. DNA constructs or cassettes for expression in plants were constructed using such artificial coding sequences and subsequently introduced into plant transformation vectors. Corn and cotton plants were transformed with these expression cassettes, and R0 and F1 plants of corn and cotton were tested for Coleopteran and/or Hemipteran resistance.

For the purposes of this disclosure, any transgenic, recombinant, chimeric or artificial nucleotide sequence would be considered to be an isolated nucleotide sequence since these are not naturally occurring sequences. A transgenic, recombinant, chimeric or artificial nucleotide sequence would be considered to be an isolated nucleotide sequence whether it is present within the plasmid, vector or construct used to transform plant cells, within the genome of the plant, or is present in detectable amounts in tissues, progeny, biological samples or commodity products derived from the plant. The nucleotide sequence or any fragment derived therefrom would therefore be considered to be isolated or isolatable if the DNA molecule can be extracted from cells, or tissues, or homogenate from a plant or seed or plant organ; or can be produced as an amplicon from extracted DNA or RNA from cells, or tissues, or homogenate from a plant or seed or plant organ, any of which is derived from such materials derived from the transgenically altered plant.

Exemplary Proteins are Related by Structure

High throughput sequencing and bioinformatics capabilities were used to screen Bt genomes for novel genes encoding Bt toxin proteins, which were then cloned and expressed in an acrystalliferous Bt strain to produce protein samples for evaluation in in vitro bioassays designed to test for insecticidal activity. Using this method, the novel genus of toxin proteins exhibiting insecticidal activity against Coleopteran and/or Hemipteran species exemplified herein by TIC3131, TIC3400 and TIC3407 was discovered.

The polypeptides/proteins of the present invention are related by source or origin (i.e., from Bt strains of bacteria), by biological toxin activity against insect pests within the orders Coleoptera and/or Hemiptera, by primary structure (conserved amino acid sequences), and by length (from about 250 to about 300 amino acids). Proteins of the present invention, and proteins that resemble the proteins of the present invention, can be identified by comparison to each other using various computer based algorithms known in the art (see Table 1). Amino acid identities reported herein are a result of a Clustal W alignment using these default parameters: Weight matrix: blosum, Gap opening penalty: 10.0, Gap extension penalty: 0.05, Hydrophilic gaps: On, Hydrophilic residues: GPSNDQERK, Residue-specific gap penalties: On (Thompson, et al (1994) Nucleic Acids Research, 22:4673-4680). Other alignment algorithms are also available in the art and provide results similar to those obtained using a Clustal W alignment.

It is intended that a polypeptide exhibiting insect inhibitory activity against a Coleopteran and/or Hemipteran insect species is within the scope of the present invention if an alignment of the polypeptide with any of SEQ ID NO:2 (TIC3131), SEQ ID NO:4 (TIC3400) and/or SEQ ID NO:6 (TIC3407) results in at least 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282 or 283 amino acid identities. That is, in certain embodiments, the polypeptide of the present invention comprises an amino acid sequence exhibiting at least 141-283 amino acid identities when compared to SEQ ID NO:2, SEQ ID NO:4 or SEQ ID NO:6.

It is also intended that a protein exhibiting insect inhibitory activity is within the scope of the present invention if the protein is used in a query, e.g., in a Clustal W alignment, and at least one of the proteins of the present invention as set forth as TIC3131, TIC3400 and TIC3407 are identified as hits in such alignment in which the query protein exhibits at least about 76 to about 100% identity along the length of the query protein (i.e., see Table 2).

TABLE 1

Pair-wise matrix display of exemplary proteins
Matrix of pairwise sequence identities

| | (N) | | | | | | |
|---|---|---|---|---|---|---|---|
| (M) | 8 | 10 | 2 | 4 | 6 | 12 | 14 |
| TIC2807 | — | 68.2 | 66.1 | 63.9 | 62.5 | 66.4 | 57.9 |
| (SEQ ID NO: 8) | | (191) | (185) | (179) | (175) | (186) | (162) |
| TIC2808 | 70 | — | 63 | 63.4 | 64.1 | 63 | 56 |
| (SEQ ID NO: 10) | (191) | | (172) | (173) | (175) | (172) | (153) |
| TIC3131 | 68.8 | 63.9 | — | 78.1 | 64.3 | 62.8 | 53.2 |
| (SEQ ID NO: 2) | (185) | (172) | | (210) | (173) | (169) | (143) |
| TIC3400 | 66.5 | 64.3 | 78.1 | — | 65.8 | 66.2 | 54.6 |
| (SEQ ID NO: 4) | (179) | (173) | (210) | | (177) | (178) | (147) |
| TIC3407 | 64.6 | 64.6 | 63.8 | 65.3 | — | 62.7 | 52 |
| (SEQ ID NO: 6) | (175) | (175) | (173) | (177) | | (170) | (141) |
| TIC3093 | 65.7 | 60.8 | 59.7 | 62.9 | 60.1 | — | 53.7 |
| (SEQ ID NO: 12) | (186) | (172) | (169) | (178) | (170) | | (152) |
| TIC2019 | 59.3 | 56 | 52.4 | 53.8 | 51.6 | 55.7 | — |
| (SEQ ID NO: 14) | (162) | (153) | (143) | (147) | (141) | (152) | |

Table 1: Column (M) refers to SEQ ID NO: and TIC#; Columns under (N) refer to SEQ ID NO:
The percent amino acid identity between all pairs is calculated relative to (M) and is represented by the upper numbers.
The lower number in each box in the matrix represents the number of identical amino acids between the pair.

Exemplary Proteins are Related by Function

In certain embodiments, the pest is specifically an insect pest. Insect pests include insects selected from the orders Coleoptera, Diptera, Hymenoptera, Lepidoptera, Mallophaga, Homoptera, Hemiptera, Blattodea, Orthoptera, Thysanoptera, Dermaptera, Isoptera, Anoplura, Siphonaptera, and Trichoptera.

The insects of the order Coleoptera, are intended to include but are not limited to, *Agriotes* spp., *Anthonomus* spp., *Atomaria linearis, Chaetocnema tibialis, Cosmopolites* spp., *Curculio* spp., *Dermestes* spp., *Diabrotica* spp., *Epilachna* spp., *Eremnus* spp., *Leptinotarsa decemlineata, Lissorhoptrus* spp., *Melolontha* spp., *Orycaephilus* spp., *Otiorhynchus* spp., *Phlyctinus* spp., *Popillia* spp., *Psylliodes* spp., *Rhizopertha* spp., *Scarabeidae, Sitophilus* spp., *Sitotroga* spp., *Tenebrio* spp., *Tribolium* spp. and *Trogoderma* spp, particularly when the pest is *Diabrotica virgifera* virgifera (Western Corn Rootworm, WCR), *Diabrotica barberi* (Northern Corn Rootworm, NCR), *Diabrotica virgifera zeae* (Mexican Corn Rootworm, MCR), *Diabrotica balteata* (Brazilian Corn Rootworm, BZR), *Diabrotica undecimpunctata howardii* (Southern Corn Rootworm, SCR), and a Brazilian Corn Rootworm complex (BCR) consisting of *Diabrotica viridula* and *Diabrotica speciosa.*

The insects can also include adults and nymphs of the order Hemiptera, such as but not limited to, plant bugs from the Family Miridae, cicadas from the Family Cicadidae, leafhoppers (e.g., *Empoasca* spp.) from the Family Cicadellidae, planthoppers from the families Fulgoroidea and Delphacidae, treehoppers from the Family Membracidae, psyllids from the Family Psyllidae, whiteflies from the Family Aleyrodidae, aphids from the Family Aphididae, phylloxera from the Family Phylloxeridae, mealybugs from the Family Pseudococcidae, scales from the families Coccidae, Diaspididae and Margarodidae, lace bugs from the Family Tingidae, stink bugs from the Family Pentatomidae, cinch bugs (e.g., *Blissus* spp.) and other seed bugs from the Family Lygaeidae, spittlebugs from the Family Cercopidae, squash bugs from the Family Coreidae, and red bugs and cotton stainers from the Family Pyrrhocoridae. Other pests from the order Hemiptera include *Acrosternum hilare* (green stink bug), *Anasa tristis* (squash bug), *Blissus leucopterus leucopterus* (chinch bug), *Corythuca gossypii* (cotton lace bug), *Cyrtopeltis modesta* (tomato bug), *Dysdercus suturellus* (cotton stainer), *Euschistus servus* (brown stink bug), *Euschistus variolarius* (one-spotted stink bug), *Graptostethus* spp. (complex of seed bugs), *Leptoglossus corculus* (leaf-footed pine seed bug), *Lygus lineolaris* (tarnished plant bug), *Lygus hesperus* (Western tarnish plant bug), *Nezara viridula* (southern green stink bug), *Oebalus pugnax* (rice stink bug), *Oncopeltus fasciatus* (large milkweed bug), and *Pseudatomoscelis seriatus* (cotton fleahopper).

In certain embodiments, the recombinant polypeptide of the present invention exhibits insect inhibitory activity against Coleopteran species selected from the group consisting of *Agriotes* spp., *Anthonomus* spp., *Atomaria linearis, Chaetocnema tibialis, Cosmopolites* spp., *Curculio* spp., *Dermestes* spp., *Diabrotica* spp., *Epilachna* spp., *Eremnus* spp., *Leptinotarsa decemlineata, Lissorhoptrus* spp., *Melolontha* spp., *Orycaephilus* spp., *Otiorhynchus* spp., *Phlyctinus* spp., *Popillia* spp., *Psylliodes* spp., *Rhizopertha* spp., Scarabeidae, *Sitophilus* spp., *Sitotroga* spp., *Tenebrio* spp., *Tribolium* spp. and *Trogoderma* spp, particularly when the pest is *Diabrotica virgifera virgifera* (Western Corn Rootworm, WCR), *Diabrotica barberi* (Northern Corn Rootworm, NCR), *Diabrotica virgifera zeae* (Mexican Corn Rootworm, MCR), *Diabrotica balteata* (Brazilian Corn Rootworm (BZR), *Diabrotica undecimpunctata howardii* (Southern Corn Rootworm, SCR), and a Brazilian Corn Rootworm complex (BCR) consisting of *Diabrotica viridula* and *Diabrotica speciosa.*

The proteins of the present invention represent a new Cry family, exhibiting no greater than 76% amino acid sequence identity to any other Bt protein known in the art. The protein exhibiting the nearest identity to any of the proteins of the present invention is AXMI108 (SEQ ID NO:102 in WO2009158470; Accession: HC309919). AXMI108 is 90% identical to Cry45Aa1 (GI:56744212, ACCESSION: AB180980) (Okumura, et al.; Protein Expr. Purif. 47 (1), 144-151 (2006), "Efficient solubilization, activation, and purification of recombinant Cry45Aa of *Bacillus thuringiensis* expressed as inclusion bodies in *Escherichia coli*"). AXMI108 and Cry45Aa1 were aligned using Clustal W to each protein exemplified in the present invention and the results are shown in Table 2.

TABLE 2

Alignment of proteins to AXMI108 and Cry45Aa1

| Protein | Amino acid identities* with AXMI108 | Percent amino acid identity* with AXMI108 | Amino acid identities* with Cry45Aa1 | Percent amino acid identity* with Cry45Aa1 |
|---|---|---|---|---|
| TIC3131 (SEQ ID NO: 2) | 202 | 75.1% | 197 | 73.2% |
| TIC3400 (SEQ ID NO: 4) | 186 | 69.1% | 188 | 69.9% |
| TIC3407 (SEQ ID NO: 6) | 167 | 61.6% | 167 | 61.6% |
| Cry45Aa1 (SEQ ID NO: 16) | 249 | 90.5% | 275 | 100% |
| AXMI108 (SEQ ID NO: 18) | 278 | 100% | 249 | 89.6% |

*in a Clustal W alignment

In one embodiment, exemplary proteins described herein are related by common function and exhibit insecticidal activity towards Coleoptera and/or Hemiptera insect species. Table 3 correlates the proteins to pesticidal activity by insect species. Blank spaces in the table indicate that the insect species was either not tested, or no activity was observed under the test conditions.

TABLE 3

Activity profiles of exemplary proteins

| | WCR | SCR | CPB | TPB | WTPB |
|---|---|---|---|---|---|
| TIC3131 | M/S/R | M/S | M/S | M/S | M/S |
| TIC3400 | /R | | M/S | M/S | S |
| TIC3407 | S/R | | M/S | | |

M = Mortality observed (compared to control)
S = Stunting observed on survivors (compared to control)
R = root protection observed in F1 corn plants The results show that the proteins described herein exhibit insect inhibitory activities against an insect pest from the order Coleoptera and/or the order Hemiptera including applicable adults, pupae, larvae, and neonates. Specifically, TIC3131 exhibited activity against WCR, SCR, CPB, TPB and WTPB; TIC3400 exhibited activity against WCR, CPB, TPB and WTPB, and TIC3407 exhibited activity against WCR and CPB.

Identification of Protein-Encoding Sequences

TIC3131, TIC3400 or TIC3407 protein-encoding sequences and sequences having at least 62 to 100% nucleotide sequence identity including any percentage of the intervening range (i.e., 62, 53, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%) identity can be identified using methods such as thermal amplification, hybridization, and the like. See, for example, Sambrook and Russell (2001) *Molecular Cloning: A Laboratory Manual*. (Cold Spring Harbor Laboratory Press, Cold Spring Harbor, N.Y.) and Innis, et al. (1990) *PCR Protocols: A Guide to Methods and Applications* (Academic Press, NY).

In one embodiment, exemplary polynucleotides that encode insect inhibitory TIC3131, TIC3400 or TIC3407 proteins exhibit the nucleotide sequences set forth in SEQ ID NO:1, 3 or 5, including these sequences when operably linked to a heterologous promoter. Nucleotide sequences encoding these proteins can be used as probes and primers for screening to identify other members of the genus using thermal or isothermal amplification and/or hybridization methods, e.g., oligonucleotides from the sequences as set forth in SEQ ID NOs:19, 20 or 21, and oligonucleotides hybridizing to sequences disclosed herein.

TIC3131, TIC3400 or TIC3407 Protein and Biological Equivalents

The proteins disclosed herein can also be used to produce antibodies that bind specifically to this genus of proteins and can be used to screen for and to find other members of the genus.

An aspect of the invention is to provide methods for discovering related proteins, and such methods include the sequencing of Bt genomes, assembly of sequence data, the identification and cloning of Bt genes encoding such pesticidal proteins, and the expression and testing of new Bt proteins to assay for pesticidal activity. In one embodiment, the proteins disclosed herein include functionally equivalent fragments (N- or C-terminal deletions) of the proteins disclosed herein.

Peptides, polypeptides, and proteins that are biologically functionally equivalent to TIC3131, TIC3400 or TIC3407 include, but are not limited to, amino acid sequences containing conservative amino acid substitutions in the TIC3131, TIC3400 or TIC3407 protein sequences. In such amino acid sequences, one or more amino acids in the sequence is (are) substituted with another amino acid(s), resulting in a silent change.

While the insect inhibitory polypeptides disclosed herein preferably comprise the TIC3131, TIC3400 or TIC3407 protein sequence, fragments and variants of these sequences possessing the same or substantially similar insect inhibitory activity are also within the scope of the present invention. For example, toxin proteins having at least about 221 or more contiguous amino acids identical to such a contiguous length of amino acids in a TIC3131, TIC3400 or TIC3407 protein and which exhibit insect inhibitory activity are also provided herein.

In some embodiments, fragments of the TIC3131, TIC3400 or TIC3407 protein can be truncated forms wherein one or more amino acids are deleted from the N-terminal end, C-terminal end, the middle of the protein, or combinations thereof with insect inhibitory activity. These fragments can be naturally occurring or synthetic mutants of TIC3131, TIC3400 or TIC3407, and retain the insect inhibitory activity of TIC3131, TIC3400 or TIC3407. A truncated derivative having insect inhibitory activity is a TIC3131, TIC3400 or TIC3407 protein corresponding to amino acid residues 12 to 240.

Yet in another embodiment, truncated N-terminal or C-terminal deletion variants include, but are not limited to, TIC3131, TIC3400 or TIC3407 proteins that lack amino acid residues from either the N-terminus and/or the C-terminus of the toxic core of TIC3131, TIC3400 or TIC3407 proteins. For example, 1 to 11 N-terminal amino acid residues of a TIC3131, TIC3400 or TIC3407 protein can be deleted resulting in a toxin protein having amino acids 12-240 of SEQ ID NO:2. A C-terminal amino acid deletion variant toxin of a TIC3131, TIC3400 or TIC3407 protein is provided having C-terminal amino acid residues 1-6 deleted from any of SEQ ID NO:2, 4 or 6. In other embodiments, a TIC3131, TIC3400 or TIC3407 protein with corresponding amino acid residues 12 to 240 of SEQ ID NOs:2, 4 or 6 and a C-terminal truncation of 1 to 6 carboxy terminal residues of a TIC3131, TIC3400 or TIC3407 protein corresponding to residues 12 to 240 of SEQ ID NO:2, 4 or 6 are provided.

The fragments and variants of a TIC3131, TIC3400 or TIC3407 protein encompassed by the present invention possess about 62% or greater sequence identity, about 65%, 70%, 75%, 80%, 85%, 90%, 92%, 95%, 97%, 98%, or greater sequence identity, and about 99%, 99.1%, 99.2%, 99.3%, 99.4%, 99.5%, 99.6%, 99.7%, 99.8%, 99.9% or 100% amino acid sequence identity, to the corresponding amino acid sequences shown in residues 12 to 240 of SEQ ID NO:2, 4 or 6.

DNA Constructs, Plasmids, Vectors

An embodiment of the invention includes polynucleotide molecules/compositions that encode TIC3131, TIC3400 or TIC3407 protein. In certain embodiments, TIC3131, TIC3400 or TIC3407 proteins can be expressed with a recombinant DNA construct, which comprises a polynucleotide molecule with the open reading frame encoding the protein operably linked to elements such as a heterologous promoter and any other regulatory element functional for expression in the system for which the construct is intended. For example, plant-functional promoters can be operably linked to the TIC3131, TIC3400 or TIC3407 protein-encoding sequences for expression of the protein in plants and Bt-functional promoters can be operably linked to TIC3131, TIC3400 or TIC3407 protein-encoding sequences for expression of the protein in Bt. Other useful elements that can be operably linked to the TIC3131, TIC3400 or TIC3407 protein-encoding sequences include, but are not limited to, enhancers, introns, leaders, encoded protein immobilization tags (HIS-tag), encoded sub-cellular translocation peptides (i.e., plastid transit peptides, signal peptides), encoded polypeptide sites for post-translational modifying enzymes, ribosomal binding sites, and RNAi target sites.

Exemplary polynucleotide molecules/compositions provided herein include, but are not limited to, SEQ ID NO:1, SEQ ID NO:3, and SEQ ID NO:5. The codons of a polynucleotide molecule/composition coding for proteins of the present invention can be substituted for synonymous codons (also called a silent substitution); and are within the scope of the present invention. Modified polynucleotides encoding any of the TIC3131, TIC3400 or TIC3407 proteins disclosed herein are thus provided.

A recombinant DNA construct comprising TIC3131, TIC3400 or TIC3407 protein-encoding sequences can also further comprise a region of DNA that encodes for one or more insect inhibitory agents which can be configured to contemporaneously express or co-express with a DNA sequence encoding a protein different from a TIC3131, TIC3400 or TIC3407, an insect inhibitory dsRNA molecule, or an ancillary protein. Ancillary proteins include co-factors, enzymes, binding-partners, or other insect inhibitory agents that function synergistically to aid in the effectiveness of an insect inhibitory agent, e.g., by aiding its expression, influencing its stability in plants, optimizing free energy for oligomerization, augmenting its toxicity, and increasing its spectrum of activity.

A recombinant DNA construct can be assembled so that all proteins or dsRNA molecules are expressed from one promoter or each protein or dsRNA molecules is under separate promoter control or some combination thereof. The proteins of this invention can be expressed from a multi-gene expression system in which one or more proteins of the present invention are expressed from a common nucleotide segment which also contains other open reading frames and/or promoters depending on the type of expression system selected. For example, a bacterial multi-gene expression system can utilize a single promoter to drive expression of multiply-linked/tandem open reading frames from within a single operon (i.e., polycistronic expression). In another example, a plant multi-gene expression system can utilize multiply-linked expression cassettes each expressing a different protein or other agent such as one or more dsRNA molecules. Still in another example, a plant multi-gene expression system can utilize multiply-unlinked expression cassettes each expressing a different protein or other agent such as one or more dsRNA molecules.

In certain embodiments, the polynucleotide molecule/composition or recombinant DNA construct comprising a TIC3131, TIC3400 or TIC3407 protein-encoding sequence can be delivered to host cells by vectors, e.g., a plasmid, baculovirus, artificial chromosome, virion, cosmid, phagemid, phage, or viral vector. Such vectors can be used to achieve stable or transient expression of a TIC3131, TIC3400 or TIC3407 protein-encoding sequence in a host cell and result in subsequent translation to protein. An exogenous polynucleotide or a DNA construct that comprises a TIC3131, TIC3400 or TIC3407 protein-encoding sequence and that is introduced into a host cell is also referred to herein as a "transgene."

Transgenic Host Cells, Plant Cells, Plants and Plant Parts

Further provided herein are transgenic bacteria, transgenic plant cells, transgenic plants, and transgenic plant seed and other plant parts that contain any polynucleotide (i.e., transgene) that expresses any one or more of the TIC3131, TIC3400 and TIC3407 protein-encoding sequences provided herein. It is intended that "bacterial cell" or "bacterium" can include, but are not limited to, an *Agrobacterium*, a *Bacillus*, an *Escherichia*, a *Salmonella*, a *Pseudomonas*, or a *Rhizobium* cell. It is intended that "plant cell" or "plant" include an alfalfa, banana, barley, bean, broccoli, cabbage, *brassica*, carrot, cassava, castor, cauliflower, celery, chickpea, Chinese cabbage, citrus, coconut, coffee, corn, clover, cotton, a cucurbit, cucumber, Douglas fir, eggplant, eucalyptus, flax, garlic, grape, hops, leek, lettuce, Loblolly pine, millets, melons, nut, oat, olive, onion, ornamental, palm, pasture grass, pea, peanut, pepper, pigeonpea, pine, potato, poplar, poppy, pumpkin, Radiata pine, radish, rapeseed, rice, rootstocks, rye, safflower, shrub, sorghum, Southern pine, soybean, spinach, squash, strawberry, sugar beet, sugarcane, sunflower, sweet corn, sweet gum, sweet potato, switchgrass, tea, tobacco, tomato, triticale, turf grass, watermelon, and wheat plant cell or plant. In certain embodiments, transgenic plants and transgenic plant parts regenerated from a transgenic plant cell are provided. In certain embodiments, the transgenic plants can be obtained from a transgenic seed. In certain embodiments, transgenic plant parts can be obtained by cutting, snapping, grinding or otherwise disassociating the part from the plant. In certain embodiments, the plant part can be a seed, a boll, a leaf, a flower, a stem, a root, or any portion thereof. In certain embodiments, a transgenic plant part provided herein is a non-regenerable portion of a transgenic plant part. As used in this context, a "non-regenerable" portion of a transgenic plant part is a portion that can not be induced to form a whole plant or that can not be induced to form a whole plant that is capable of sexual and/or asexual reproduction. In certain embodiments, a non-regenerable portion of a plant part is a portion of a transgenic seed, boll, leaf, flower, stem, or root.

Also provided herein are methods of making transgenic plants that comprise insect or Coleoptera and/or Hemiptera inhibitory amounts of a TIC3131, TIC3400 or TIC3407 protein. Such plants can be made by introducing a polynucleotide or a DNA construct that encodes any of the TIC3131, TIC3400 and TIC3407 proteins provided herein into a plant cell, and selecting a plant derived from said plant cell that expresses an insect or Coleoptera and/or Hemiptera inhibitory amount of the TIC3131, TIC3400 or TIC3407 proteins. Plants can be derived from the plant cells by regeneration, seed, pollen, or meristem transformation techniques.

Methods for transforming plants are well known in the art. Microprojectile bombardment methods are illustrated in U.S. Pat. No. 5,015,580 (soybean); U.S. Pat. No. 5,550,318 (corn); U.S. Pat. No. 5,538,880 (corn); U.S. Pat. No. 5,914,451 (soybean); U.S. Pat. No. 6,160,208 (corn); U.S. Pat. No. 6,399,861 (corn); U.S. Pat. No. 6,153,812 (wheat) and U.S. Pat. No. 6,365,807 (rice) and *Agrobacterium*-mediated transformation is described in U.S. Pat. No. 5,159,135 (cotton); U.S. Pat. No. 5,824,877 (soybean); U.S. Pat. No. 5,463,174 (canola); U.S. Pat. No. 5,591,616 (corn); U.S. Pat. No. 5,846,797 (cotton); U.S. Pat. No. 6,384,301 (soybean), U.S. Pat. No. 7,026,528 (wheat) and U.S. Pat. No. 6,329,571 (rice), US Patent Application Publication 2004/0087030 A1 (cotton), and U.S. Patent Application Publication 2001/0042257 A1 (sugar beet) and in Arencibia et al. (1998) Transgenic Res. 7:213-222 (sugarcane) and other more recent methods described in U.S. Patent Application Publications 2009/0138985A1 (soybean), 2008/0280361A1 (soybean), 2009/0142837A1 (corn), 2008/0282432 (cotton), 2008/0256667 (cotton), 2003/0110531 (wheat), U.S. Pat. No. 5,750,871 (canola), U.S. Pat. No. 7,026,528 (wheat), and U.S. Pat. No. 6,365,807 (rice).

Also provided herein is the use of a transgenic plant that expresses an insect or Coleoptera and/or Hemiptera inhibitory amount of the TIC3131, TIC3400 or TIC3407 protein to control an insect or Coleoptera and/or Hemiptera infestation. Any of the aforementioned transgenic plants can be used in methods for protecting a plant from insect or Coleoptera and/or Hemiptera infestation provided herein.

Also provided herein is the use of any of the aforementioned transgenic host cells to produce a TIC3131, TIC3400 or TIC3407 protein.

Methods for Detecting Genes and Proteins

Additional aspects of the invention include antibodies and methods for detecting polynucleotides that encode TIC3131, TIC3400 or TIC3407 protein or distinguishing fragments and segments thereof, methods for identifying additional insect inhibitory members of the protein genus of the present invention, formulations and methods for controlling insect growth and/or infestation, and methods for providing such control to plants and other recipient hosts.

In accordance with the invention, each composition, construct, cell, plant, formulation, or method provides for the industrial application of the proteins of the present invention, e.g., by increasing plant productivity through the commercial use of any of these proteins to inhibit insects and insect infestations.

It is contemplated that oligonucleotides derived from sequences as set forth in any of SEQ ID NOs:17, 18, 19 and 20 can be used to determine the presence or absence of a TIC3131, TIC3400 or TIC3407 transgene in a deoxyribonucleic acid sample derived from a commodity product. Given the sensitivity of certain nucleic acid detection methods that employ oligonucleotides, it is anticipated that oligonucleotides derived from sequences as set forth in any of SEQ ID NOs:17, 18, 19 and 20 can also be used to detect a TIC3131, TIC3400 or TIC3407 transgene in commodity products derived from pooled sources where only a fraction of the commodity product is derived from a transgenic plant containing any of SEQ ID NOs:17, 18, 19 and 20. It is further recognized that such oligonucleotides can be used to introduce nucleotide sequence variation in each of SEQ ID NOs:17, 18, 19 and 20. Such "mutagenesis" oligonucleotides are useful for identification of TIC3131, TIC3400 or TIC3407 amino acid sequence variants exhibiting a range of insect inhibitory activity and/or varied expression in transgenic plant host cells.

Plant Products and Processed Plants

In certain embodiments, a plant product can comprise commodity or other products of commerce derived from a transgenic plant or transgenic plant part, where the commodity or other products can be tracked through commerce by detecting nucleotide segments or expressed RNA or proteins that encode or comprise distinguishing portions of a TIC3131, TIC3400 or TIC3407 protein. Such commodity or other products of commerce include, but are not limited to, plant parts, biomass, oil, meal, sugar, animal feed, flour, flakes, bran, lint, processed seed, and seed.

Also provided herein are processed plant products, wherein said processed product comprises a detectable amount of a TIC3131, TIC3400 or TIC3407 protein, an insect inhibitory segment or fragment thereof, or any distinguishing portion thereof. In certain embodiments, the processed product is selected from the group consisting of plant biomass, oil, meal, animal feed, flour, flakes, bran, lint, hulls, and processed seed. In certain embodiments, the processed product is non-regenerable. In certain embodiments, a distinguishing portion thereof can comprise any one or more segments 1, 2, 3, 4, 5 and 6 of SEQ ID NO:2, 4 or 6, or a polypeptide of at least 20, 30, 50 or 100 amino acids of the amino acid sequence of SEQ ID NO:2, 4 or 6. In certain embodiments, a distinguishing portion thereof can comprise any one or more segments 1, 2, 3, 4, 5 and 6 of SEQ ID NO:2, 4 or 6, or any polypeptide of at least 20, 30, 50 or 100 amino acids of SEQ ID NO:2, 4 or 6.

Also provided herein are processed plant products, which comprise a detectable amount of a polynucleotide or a DNA construct encoding a TIC3131, TIC3400 or TIC3407 protein, a segment thereof, an insect inhibitory fragment thereof, or any distinguishing portion thereof. In certain embodiments, the processed product is selected from the group consisting of plant biomass, oil, meal, animal feed, flour, flakes, bran, lint, hulls, and processed seed. In certain embodiments, the processed product is non-regenerable.

Methods for Controlling Insects

Also provided herein are methods of controlling insects. In certain embodiments, Hemiptera and/or Coleoptera infestations of crop plants are controlled. Such methods can comprise growing a plant comprising an insect or Hemiptera and/or Coleoptera inhibitory amount of a TIC3131, TIC3400 or TIC3407 protein. In certain embodiments, such methods can further comprise any one or more of: (i) applying any composition comprising or encoding a TIC3131, TIC3400 or TIC3407 protein to the plant or a seed that gives rise to the plant; and/or (ii) transforming the plant or a plant cell that gives rise to the plant with a polynucleotide or a DNA construct encoding a TIC3131, TIC3400 or TIC3407 protein. In certain embodiments, the plant is a transiently or stably transformed transgenic plant comprising a transgene that expresses an insect or Hemiptera and/or Coleoptera inhibitory amount of a TIC3131, TIC3400 or TIC3407 protein. In certain embodiments, the plant is a non-transgenic plant to which a composition comprising a TIC3131, TIC3400 or TIC3407 protein has been applied. In certain embodiments of such methods, the plant is a corn or sugarcane plant. In certain embodiments, the Hemiptera and/or Coleoptera species is *Diabrotica* species (WCR and SCR), (CPB), WTPB and TPB. In certain embodiments, the Hemiptera and/or Coleoptera species is in a crop field.

Enrichment of the proteins of the present invention either in plants or by a process that includes culturing recombinant Bt cells under conditions to express/produce recombinant polypeptide/proteins of the present invention is contemplated. Such a process can include preparation by desiccation, lyophilization, homogenization, extraction, filtration, centrifugation, sedimentation, or concentration of a culture of recombinant Bt cells expressing/producing said recombinant polypeptide. Such a process can result in a Bt cell extract, cell suspension, cell homogenate, cell lysate, cell supernatant, cell filtrate, or cell pellet. By obtaining the recombinant polypeptides or proteins so produced, a composition that includes the recombinant polypeptides or proteins can include bacterial cells, bacterial spores, and parasporal inclusion bodies and can be formulated for various uses, including agricultural insect inhibitory spray products or as insect inhibitory formulations in diet bioassays.

It is intended that an insect inhibitory composition/formulation comprising the aforementioned recombinant polypeptide/protein is within the scope of the present invention. In certain embodiments, such composition can further comprise at least one additional polypeptide that exhibits insect inhibitory activity against the same Hemiptera and/or Coleoptera insect species but is different from the recombinant polypeptide to provide for a decreased incidence of Coleopiteran and/or Hemipteran insect resistance to the TIC3131, TIC3400 or TIC3407 protein or other Hemiptera and/or Coleoptera insect inhibitory composition. Such polypeptide is selected from the group consisting of an insect inhibitory protein, an insect inhibitory dsRNA molecule, and an ancillary protein. One example for the use of such ribonucleotide sequences to control insect pests is described in U.S. Patent Application Publication No. 2006/0021087. Examples of other such compositions include, but are not limited to, Cry1A proteins (U.S. Pat. No. 5,880,275), Cry1B (U.S. patent application Ser. No. 10/525,318), Cry1C (U.S. Pat. No. 6,033,874), Cry1F, Cry1A/F chimeras (U.S. Pat. Nos. 7,070,982; 6,962,705; and 6,713,063), and a Cry2Ab protein (U.S. Pat. No. 7,064,249).

In other embodiments, such composition may further comprise at least one additional polypeptide that exhibits insect inhibitory activity to an insect that is not inhibited by an otherwise insect inhibitory TIC3131, TIC3400 or TIC3407 protein to expand the spectrum of insect inhibition obtained. For example, for the control of Coleopteran pests, combinations of insect inhibitory TIC3131, TIC3400 or TIC3407 proteins with Coleopteran-active proteins such as Cry3Bb (U.S. Pat. No. 6,501,009) are specifically contemplated.

The potential for insects to develop resistance to certain insecticides is well documented. One insect resistance management strategy can employ transgenic crops that express two distinct insect inhibitory agents that operate through different modes of action. In this case, any insects with resistance to either one of the insect inhibitory agents will be controlled by the other insect inhibitory agent, thus reducing the chances of resistance developing in the insect population. Another insect resistance management strategy employs the use of plants that are not protected to the Hemiptera and/or Coleoptera pest species to provide a refuge for such unprotected plants. One such example is described in U.S. Pat. No. 6,551,962.

Other compositions are contemplated for combining with the proteins of the present invention, or with the combinations of proteins provided above. For example, topically applied pesticidal chemistries that are designed for controlling pests that are also controlled by the proteins of the present invention can be used with the proteins of the present invention in seed treatments, spray on/drip on/or wipe on formulations that can be applied directly to the soil (a soil drench), applied to growing plants expressing the proteins of the present invention, or formulated to be applied to seed containing one or more transgenes encoding one or more of the proteins of the present invention. Such formulations for use in seed treatments can be applied with various stickers and tackifiers known in the art. Such formulations can contain pesticides that are synergistic in mode of action with the proteins of the present invention, meaning that the formulation pesticides act through a different mode of action to control the same or similar pests that are controlled by the proteins of the present invention, or that such pesticides act to control pests within a broader host range, such as Hemiptera and/or Coleoptera species or other plant pest species such as Lepidopteran species that are not effectively controlled by the proteins of the present invention.

The aforementioned composition/formulation can further comprise an agriculturally-acceptable carrier, such as a bait, a powder, dust, pellet, granule, spray, emulsion, a colloidal suspension, an aqueous solution, a *Bacillus* spore/crystal preparation, a seed treatment, a recombinant plant cell/plant tissue/seed/plant transformed to express one or more of the proteins, or bacterium transformed to express one or more of the proteins. Depending on the level of insect inhibitory or insecticidal inhibition inherent in the recombinant polypeptide and the level of formulation to be applied to a plant or diet assay, the composition/formulation can include various by weight amounts of the recombinant polypeptide, e.g., from 0.0001% to 0.001% to 0.01% to 1% to 99% by weight of the recombinant polypeptide.

The proteins of the invention can be combined in formulations for topical application to plant surfaces, to the soil, in formulations for seed treatments, in formulations with other agents toxic to the target pests of Hemiptera and/or Coleoptera species. Such agents include but are not limited to, Hemipteran specific toxins TIC807 and variants thereof, TIC853 and variants thereof, AXMI108 and variants thereof, and Cry45Aa1 and variants thereof, and various Coleopteran specific toxins Cry3A and mCry3A, Cry3B, Cry34/35, eHIP, and 5307 toxin proteins.

In one embodiment, the present invention provides a recombinant polypeptide exhibiting inhibitory activity against Coleopteran and/or Hemipteran pest species, comprising an amino acid sequence exhibiting:

(a) at least 76% amino acid identity to SEQ ID NO:2 (TIC3131);

(b) at least 70% amino acid identity to SEQ ID NO:4 (TIC3400); or (c) at least 62% amino acid identity to SEQ ID NO:6 (TIC3407).

In a preferred embodiment, the recombinant polypeptide comprises an amino acid sequence exhibiting at least 95% identity to SEQ ID NO:2, SEQ ID NO:4 or SEQ ID NO:6; or comprises the amino acid sequence as set forth in SEQ ID NO:2 from positions 12-240, SEQ ID NO:4 from positions 12-240, or SEQ ID NO:6 from position 12-240.

In another preferred embodiment, the Coleopteran pest species is VCR, SCR, or CPB, and the Hemipteran pest species is WTPB or TPB, e.g., *Lygus hesperus* or *Lygus lineolaris* insects.

In another embodiment, there is provided an insect inhibitory composition comprising the aforementioned recombinant polypeptide, which may further comprise at least one other pesticidal agent that is different from the recombinant polypeptide, e.g., a pesticidal agent selected from the group consisting of an insect inhibitory protein, an insect inhibitory dsRNA molecule, and an ancillary protein. The pesticidal agent exhibits activity against one or more pest species of the order Lepidoptera, Coleoptera or Hemiptera and can be selected from the group consisting of Cry1A, Cry1Ab, Cry1Ac, Cry1A.105, Cry1B, Cry1C, Cry1D, Cry1E, Cry1F, Cry1G, Cry1H, Cry1I, Cry1J, Cry1K, Cry1L, Cry2A, Cry2Ab, Cry3, Cry3B, Cry4B, Cry6, Cry7, Cry8, Cry9, Cry15, Cry34, Cry35, Cry43A, Cry43B, Cry51Aa1, ET29, ET33, ET34, ET35, ET66, ET70, ET1201, TIC400, TIC407, TIC431, TIC800, TIC807, TIC834, TIC901, TIC1201, TIC1415, VIP3A and VIP3B.

In another embodiment, there is provided a method of controlling a Coleopteran and/or Hemipteran species pest by contacting the pest with an insect inhibitory amount of the aforementioned insect inhibitory composition.

Still further provided in the present invention is a DNA construct that comprises a polynucleotide operably linked to a heterologous promoter, which polynucleotide encodes an insecticidal polypeptide or insecticidal fragment thereof active against a Coleopteran and/or Hemipteran species pest. The insecticidal polypeptide comprises an amino acid sequence exhibiting (a) at least 76% amino acid identity to SEQ ID NO:2 (TIC3131);

(b) at least 70% amino acid identity to SEQ ID NO:4 (TIC3400); or (c) at least 62% amino acid identity to SEQ ID NO:6 (TIC3407).

For instance, the polynucleotide comprises a nucleotide sequence selected from the group consisting of SEQ ID NO:1, SEQ ID NO:3, SEQ ID NO:5, SEQ ID NO:19, SEQ ID NO:20 and SEQ ID NO:21. The DNA construct can further comprise a nucleotide sequence encoding at least one other pesticidal agent that is different from said recombinant polypeptide and selected from the group consisting of a Cry1A, Cry1Ab, Cry1Ac, Cry1A.105, Cry1B, Cry1C, Cry1D, Cry1E, Cry1F, Cry1G, Cry1H, Cry1I, Cry1J, Cry1K, Cry1L, Cry2A, Cry2Ab, Cry3, Cry3B, Cry4B, Cry6, Cry7, Cry8, Cry9, Cry15, Cry34, Cry35, Cry43A, Cry43B, Cry51Aa1, ET29, ET33, ET34, ET35, ET66, ET70, ET1201, TIC400, TIC407, TIC431, TIC800, TIC807, TIC834, TIC853, TIC901, TIC1201, TIC1415, VIP3A and VIP3B protein. Such pesticidal agent is toxic to a Coleopteran pest species, a Lepidopteran pest species; or a Hemipteran pest species.

Still further provided in the present invention is a plant, plant cell, plant part or seed that comprises the aforementioned DNA construct. The suitable plant/plant cell includes, but is not limited to, alfalfa, banana, barley, bean, broccoli, cabbage, *brassica*, carrot, cassava, castor, cauliflower, celery, chickpea, Chinese cabbage, citrus, coconut, coffee, corn, clover, cotton, a cucurbit, cucumber, Douglas fir, eggplant, eucalyptus, flax, garlic, grape, hops, leek, lettuce, Loblolly pine, millets, melons, nut, oat, olive, onion, ornamental, palm, pasture grass, pea, peanut, pepper, pigeonpea, pine, potato, poplar, poppy, pumpkin, Radiata pine, radish, rapeseed, rice, rootstocks, rye, safflower, shrub, sorghum, Southern pine, soybean, spinach, squash, strawberry, sugar beet, sugarcane, sunflower, sweet corn, sweet gum, sweet potato, switchgrass, tea, tobacco, tomato, triticale, turf grass, watermelon, and wheat plant or plant cell. Suitable plant part includes, but is not limited to, a seed, a boll, a leaf, a flower, a stem, and a root. The plant cell, plant or plant part is optionally grown in a field.

Still further provided in the present invention is a commodity product produced from the aforementioned plant cell, plant or plant part. Such commodity product comprises a detectable amount of the DNA construct and is selected from the group consisting of commodity corn bagged by a grain handler, corn flakes, corn cakes, corn flour, corn meal, corn syrup, corn oil, corn silage, corn starch, corn cereal, and the like.

Still further provided in the present invention is a recombinant microorganism comprising the aforementioned DNA construct. As used herein, "microorganism" shall refer to an organism that is microscopic. An organism is any living thing capable of response to stimuli, reproduction, growth and development, and maintenance of homeostasis as a stable whole. Microscopic indicates something that is usually too small to be seen by the naked human eye and as such is visible only with the use of a microscope. Microorganisms are found in all the taxonomic kingdoms (Animalia, Plantae, Fungi, Protista, and Archaea/Bacteria/Monera). Most microorganisms are unicellular, but this is not universal, since some multicellular organisms are microscopic. The term therefore indicates size and a capacity for independent existence, and is not bound by taxonomy, cellular complexity, or origin. A plant cell is a living organism capable of responding to stimuli, reproducing through cellular division, growing and developing, and maintaining cellular homeostasis. A plant cell is also usually visible only with the use of a microscope. As such, a plant cell is recognizable and routinely used as a microorganism under modern microbiology techniques. As used herein, a microorganism includes, but is not limited to, a bacterium, a plant cell, and a fungal cell. The bacterium may be a *Bacillus* species, an *Escherischia* species, a *Rhizobium* species, an *Agrobacterium* species, and a *Pseudomonas* species. The plant cell includes, but is not limited to, an alfalfa, banana, barley, bean, broccoli, cabbage, *brassica*, carrot, cassava, castor, cauliflower, celery, chickpea, Chinese cabbage, citrus, coconut, coffee, corn, clover, cotton, canola, cucurbit, cucumber, Douglas fir, eggplant, eucalyptus, flax, garlic, grape, hops, leek, lettuce, Loblolly pine, millets, melons, nut, oat, olive, onion, ornamental, palm, pasture grass, pea, peanut, pepper, pigeonpea, pine, potato, poplar, pumpkin, Radiata pine, radish, rapeseed, rice, rootstocks, rye, safflower, shrub, sorghum, Southern pine, soybean, spinach, squash, strawberry, sugar beet, sugarcane, sunflower, sweet corn, sweet gum, sweet potato, switchgrass, tea, tobacco, tomato, triticale, turf grass, watermelon, wheat, and vegetable plant cell.

Other features and advantages of the invention will be apparent from the following detailed description, examples, and claims.

EXAMPLES

The following disclosed embodiments are merely representative of the invention, which may be embodied in various forms. Thus, specific structural and functional details disclosed herein are not to be interpreted as limiting. It should be understood that the entire disclosure of each reference cited herein is incorporated within the disclosure of this application.

Example 1: Discovery of Insect Inhibitory Proteins

Bt strains exhibiting distinctive attributes, e.g., inferred toxicity, proteomic diversity, and morphological variations when compared with each other, were identified and prepared for genome sequencing. Genome sequence information of each such Bt strain was generated, raw sequence reads processed, contigs assembled from processed reads, open reading frames identified, and deduced amino acid sequences analyzed.

Example 2: Cloning and Expression of Insect Inhibitory Proteins

This example illustrates the cloning of polynucleotide segments encoding pesticidal proteins, and insertion into and expression in a recombinant host strain.

Nucleotide segments were obtained by amplification of the open reading frame encoding TIC3131, TIC3400 and TIC3407. Amplified nucleotide segments were inserted into a recombinant plasmid and transformed into an acrystalliferous Bt host cell or into an *E. coli* expression strain, and the resulting recombinant strains were observed to express a recombinant protein.

Recombinant proteins exemplified herein were observed to exhibit pesticidal properties to a variety of pest species (as described in Examples 3-10 below). Nucleotide segments exhibiting nucleotide sequence as set forth in SEQ ID NO:1, SEQ ID NO:3 and SEQ ID NO:5 were confirmed to encode proteins having amino acid sequences as set forth in SEQ ID NO:2 (TIC3131), SEQ ID NO:4 (TIC3400) and SEQ ID NO:6 (TIC3407), respectively.

Example 3: Coleopteran Activity of TIC3131, TIC3400 and TIC3407

This example illustrates the Coleoptera activity exhibited by TIC3131, TIC3400 and TIC3407 proteins when provided in an insect diet and fed to Western Corn Rootworm (WCR), Southern Corn Rootworm (SCR) and Colorado Potato Beetle (CPB).

Spore/crystal preparations containing the toxin protein in TX buffer (i.e., 10 mM Tris, 0.005% TritonX100 and 0.1 mM EDTA) was analyzed by SDS-PAGE and quantified using spot densitometry. Bt spore/crystal preparations were submitted for insect diet-overlay bioassays against WCR, SCR and CPB.

For the WCR and SCR bioassay, 200 mL of WCR diet was prepared in a manner similar to that described by Pleau, et al. (M. J. Pleau, J. E. Huesing, G. P. Head, D. F. Feir, "Development of an artificial diet for the western corn rootworm", Entomol. Exp. Appl. 105:1-11 (2002)). Twenty (20) μL of test sample were applied per well. Plates were allowed to dry before adding insect larvae. One WCR neonate was added per well. Plates were sealed with mylar and ventilated using an insect pin. Twenty four (24) larvae were tested per concentration. The bioassay plates were incubated at 27° C., 60% relative humidity (RH), and in complete darkness for 5-7 days. The number of surviving larvae per treatment was recorded at the end of the experiment. The masses of the surviving larvae were recorded on a microbalance (Cahn C-33). Data were analyzed using JMP® 4 statistical software (SAS Institute, Cary, N.C., USA). The results show that TIC3131 exhibited activity against WCR and SCR, and that TIC3407 exhibited activity against WCR.

For the CPB bioassay, the CPB diet consists of 13.2 g/L agar (Serva 11393), 140.6 g/L Bio-Serve pre-mix (F9380B), 4.5 ml/L KOH (18.3% w/w), and 2.5 ml/L formalin (37%). The diet was dispensed in 200 μL aliquots onto 96-well plates and dried briefly prior to sample application. Twenty (20) μL of test sample were applied per well, with sterile water serving as the untreated control (UTC). Plates were allowed to dry before adding insect larvae. One neonate CPB larva was added per well with a fine paintbrush. Plates were sealed with mylar and ventilated using an insect pin. Forty (40) larvae were tested per treatment. The bioassay plates were incubated at 27° C., 60% RH, and in complete darkness for 5-7 days. The plates were scored for larval stunting and mortality. Data were analyzed using JMP® 4 statistical software (SAS Institute, Cary, N.C., USA). The results show that TIC3131, TIC3400 and TIC3407 exhibited activity against CPB.

Example 4: Hemipteran Activity of TIC3131 and TIC3400

This example illustrates the Hemiptera activity exhibited by TIC3131, TIC3400 and TIC3407 proteins when provided in an insect diet and fed to *Lygus hesperus* (Western Tarnished Plant Bugs, WTPB) and *Lygus lineolaris* (Tarnished Plant Bugs, TPB).

Protocols for bioassays and scoring insects for mortality and stunting are know in the art, an example for WTPB and TPB bioassays is described in PCT Patent Application Publication No. WO 2012/139004. The results show that TIC3131 and TIC3400 exhibited activity against WTPB and TPB.

Example 5: Coleopteran Activity of Proteolytically Digested TIC3131

This example illustrates the Coleopteran inhibitory activity of proteolytically treated TIC3131 (Trypsin-TIC3131) having the amino acid sequence as set forth in SEQ ID NO:2 from amino acid position 2 through 254.

TIC3131 was expressed and purified as described in Example 2, and was further subjected to proteolytic processing with trypsin to form a core toxin fragment having the amino acid sequence as set forth in SEQ ID NO:2 (Trypsin-TIC3131) from amino acid position 2 through 254. This proteolytically digested sequence was confirmed by mass spectrometry.

Diet containing Trypsin-TIC3131 were infested with Coleopteran neonates and assayed for inhibitory activity in a similar way as in Example 3. Trypsin-TIC3131 exhibited activity against WCR.

Example 6: Synthesis of Genes Encoding TIC3131, TIC3400 or TIC3407 Protein for Expression in Plants Nucleotide sequences encoding a TIC3131 protein, a TIC3400 protein, and a TIC3407 protein were designed and synthesized according to methods generally described in U.S. Pat. No. 5,500,365. These nucleotide sequences are provided herein as SEQ ID NO:19, SEQ ID NO:20, and SEQ ID NO:21, respectively.

Example 7: Expression Cassettes for Expression of TIC3131, TIC3400 or TIC3407 Protein in Plants A variety of plant expression cassettes were constructed with the sequences as set forth in SEQ ID NO:19, SEQ ID NO:20 and SEQ ID NO:21. Such expression cassettes are useful for transient expression in plant protoplasts or transformation of plant cells. Typical expression cassettes were designed with respect to the eventual placement of the protein within the cell. One set of expression cassettes was designed in a manner to allow the protein to be translated and remain in the cytosol. Another set of expression cassettes was designed to have a transit peptide contiguous with the toxin protein to allow targeting to an organelle of the cell such as the chloroplast or plastid. All expression cassettes were designed to begin at the 5' end with a promoter which can be comprised of multiple promoter elements and enhancer elements contiguously linked to boost the expression of the transgene. The promoter sequence was usually followed contiguously with one or more leader sequences 3' to the promoter. An intron sequence was provided 3' to the leader sequence to improve expression of the transgene. A coding sequence for the toxin or transit peptide and coding sequence for the toxin was located 3' of the promoter, leader and intron configuration. A terminator sequence was provided 3' of the coding sequence to facilitate termination of transcription and provides sequences important for the polyadenylation of the resulting transcript. All of the elements described above were arranged contiguously with often additional sequence provided for the construction of the expression cassette such as restriction endonuclease sites or ligation independent cloning sites.

Example 8: Transformation Vectors Containing TIC3131, TIC3400 or TIC3407 Expression Cassette To construct *Agrobacterium*-mediated transformation vectors, the TIC3131, TIC3400 and TIC3407 expression cassettes were cloned into suitable vectors between the *Agrobacterium* border sequences such that they would be transferred to the genome of a host plant cell by *Agrobacterium* hosts containing the constructed vectors along with a selectable marker gene. More specifically, the restriction fragment containing the entire cytosolic expression cassette was cloned into an *Agrobacterium* plant transformation vector. Similarly, the restriction fragment containing the entire plastid targeted expression cassette was cloned into an *Agrobacterium* plant transformation vector. The vectors containing the TIC3131, TIC3400 and TIC3407 expression cassettes (i.e., untargeted cassette or targeted cassettes) were introduced into *Agrobacterium* by electroporation or by tri-parental mating.

Example 9: Hemipteran Activity of TIC3131, TIC3400 or TIC3407 in Cotton Plant

This example illustrates the toxicity of the TIC3131, TIC3400 and TIC3407 insect toxin proteins to Coleoptera and/or Hemiptera when expressed in plant tissue and provided as a diet to WCR, SCR, WTPB and TPB.

Transgenic cotton plants (recombinant cotton plants) are produced and tested for efficacy. Regenerated (R0) transgenic plants are transferred to soil and tissue samples selected from transformation events that are low in copy number and expressing TIC3131, TIC3400 or TIC3407 protein. Lyophilized tissue samples of R0 plants are weighed and combined 1:50 and 1:100 (weight:buffer) of 25 mM Sodium-carb/bicarb buffered at pH 10.5 to extract soluble protein from the tissue. Samples are confirmed by Western blot for presence of TIC3131, TIC3400 or TIC3407 protein. Sample extracts are fed to *Lygus lineolaris* and *Lygus hesperus* using the bioactivity assay described in Example 4. Extract from DP393 cotton tissue absent of TIC3131, TIC3400 or TIC3407 protein is also prepared as negative control. Sample extracts from events expressing TIC3131, TIC3400 or TIC3407 exhibit mortality against *Lygus lineolaris* and *Lygus hesperus* and survivors are stunted. Mortality and stunting scores are significant compared to bioactivity scores of insects fed with sample extracts from the DP393 negative control.

R0 plants are grown and self-pollinated to obtain seed homozygous for the introduced transgenic DNA. Homozygous plants from single copy events are selected and five (5) seed per event planted and evaluated in a whole plant caging assay. Plants are grown to flowering stage and each whole cotton plant is enclosed in a mesh cage made from perforated plastic. Two (2) pairs of male and female *Lygus hesperus* and *Lygus lineolaris* adults are placed into each cage and allowed to reproduce. Resulting insect progeny are allowed to infest the caged cotton plants for three (3) weeks. At the end of the twenty-one (21) day period, *Lygus* insects at various stages of development are counted and average means calculated on a per plant basis. Plants expressing TIC3131, TIC3400 or TIC3407 have significantly fewer surviving insects compared to the DP393 negative control.

Example 10: Coleopteran Activity of TIC3131, TIC3400 or TIC3407 in Corn Plant

This example demonstrates that recombinant plants expressing recombinant proteins of the present invention sustain significantly reduced root damage when infested by Coleopteran pests as compared to non-recombinant plants.

R0 transgenic corn plants expressing TIC3131, TIC3400 or TIC3407 were obtained by methods known in the art using vectors containing the expression cassettes from Example 7. Events that were low in copy number and express TIC3131, TIC3400 or TIC3407 protein were selected for bioassays. Plants expressing Cry3Bb proteins were used as positive controls and R0 plants which do not contain insecticidal proteins serve as negative controls.

F1 transgenic corn plants were grown from seed produced by pollinating ears of non-transformed wild-type commercial germplasm plants with pollen from R0 transformants. Plants expressing Cry3Bb as well as plants expressing both Cry3Bb and Cry34/35 binary toxin were used as positive controls; non-transgenic corn plants were used as negative control. Results are tabulated in Table 3.

After being transplanted to soil in caged pots, F1 plants were infested with 2000 WCR eggs per plant and grown to the V8 stage under controlled conditions. Root ratings were determined using the Oleson et al. rating scale of 0-3, where 0 means no injury and 3 means three or more nodes are pruned to within 1.5 inches of the stalk (J. D. Oleson, Y-L. Park, T. M. Nowatzki, J. J. Tollefson, "Node-Injury Scale to Evaluate Root Injury by Corn Rootworms", Journal of Economic Entomology, 98(1):1-8, 2005).

Plants expressing TIC3131, TIC3400 or TIC3407 had significantly less root damage from corn rootworm compared to the negative control and exhibited a root rating below 2 on average when targeted to the cytosol. Plants expressing the proteins of the present invention can be crossed by breeding with transgenic events expressing other toxin proteins and/or expressing other transgenic traits such as herbicide tolerance genes, genes conferring yield or stress tolerance traits, and the like, or such traits can be combined in a single vector so that the traits are all linked.

Having illustrated and described the principles of the present invention, it should be apparent to persons skilled in the art that the invention can be modified in arrangement and detail without departing from such principles. Those skilled

What is claimed is:

1. A DNA construct comprising a polynucleotide operably linked to a heterologous promoter, wherein said polynucleotide encodes an insecticidal polypeptide active against a Coleopteran and/or Hemipteran species pest, wherein said insecticidal polypeptide comprises the amino acid sequence as set forth in SEQ ID NO:2, SEQ ID NO:4, or SEQ ID NO:6.

2. The DNA construct of claim 1, wherein said polynucleotide comprises a nucleotide sequence selected from the group consisting of SEQ ID NO:1, SEQ ID NO:3, SEQ ID NO:5, SEQ ID NO:19, SEQ ID NO:20 and SEQ ID NO:21.

3. The DNA construct of claim 1, further comprising a nucleotide sequence encoding at least one other pesticidal agent that is different from said insecticidal polypeptide.

4. The DNA construct of claim 3, wherein said pesticidal agent is selected from the group consisting of a Cry1A, Cry1Ab, Cry1Ac, Cry1A.105, Cry1B, Cry1C, Cry1D, Cry1E, Cry1F, Cry1G, Cry1H, Cry1I, Cry1J, Cry1K, Cry1L, Cry2A, Cry2Ab, Cry3, Cry3B, Cry4B, Cry6, Cry7, Cry8, Cry9, Cry15, Cry34, Cry35, Cry43A, Cry43B, Cry51Aa1, ET29, ET33, ET34, ET66, ET70, TIC407, TIC431, TIC807, TIC834, TIC853, TIC901, TIC1201, TIC1415, VIP3A and VIP3B protein; said pesticidal agent being toxic to a Coleopteran pest species, a Lepidopteran pest species; or a Hemipteran pest species.

5. A plant cell, plant or plant part comprising the DNA construct of claim 1, wherein said polynucleotide is modified for use in plants.

6. The plant cell, plant or plant part of claim 5, wherein said plant cell or plant is selected from the group consisting of alfalfa, banana, barley, bean, broccoli, cabbage, *brassica*, carrot, cassava, castor, cauliflower, celery, chickpea, Chinese cabbage, citrus, coconut, coffee, corn, clover, cotton, a cucurbit, cucumber, Douglas fir, eggplant, *eucalyptus*, flax, garlic, grape, hops, leek, lettuce, Loblolly pine, millets, melons, nut, oat, olive, onion, ornamental, palm, pasture grass, pea, peanut, pepper, pigeonpea, pine, potato, poplar, poppy, pumpkin, *Radiata* pine, radish, rapeseed, rice, rootstocks, rye, safflower, shrub, sorghum, Southern pine, soybean, spinach, squash, strawberry, sugar beet, sugarcane, sunflower, sweet corn, sweet gum, sweet potato, switchgrass, tea, tobacco, tomato, triticale, turf grass, watermelon, and wheat plant cell or plant, and wherein said plant part is a seed, a boll, a leaf, a flower, a stem, or a root.

7. A commodity product produced from the plant cell, plant or plant part of claim 5, said commodity product comprising a detectable amount of said DNA construct, wherein said commodity product is selected from the group consisting of commodity corn bagged by a grain handler, corn flakes, corn cakes, corn flour, corn meal, corn syrup, corn oil, corn silage, corn starch, and corn cereal.

8. The plant cell, plant or plant part of claim 5, wherein said polynucleotide is selected from the group consisting of SEQ ID NO:19, SEQ ID NO:20 and SEQ ID NO:21.

* * * * *